(12) United States Patent
St. Onge et al.

(10) Patent No.: US 7,403,872 B1
(45) Date of Patent: Jul. 22, 2008

(54) METHOD AND SYSTEM FOR INSPECTING MANUFACTURED PARTS AND SORTING THE INSPECTED PARTS

(75) Inventors: James W. St. Onge, Bloomfield, MI (US); Joseph W. Priskorn, Macomb, MI (US); John D. Spalding, Ann Arbor, MI (US); John V. McKowen, Grand Blanc, MI (US); Kenneth S. Kolodge, Attica, MI (US); Brett J. Lee, Fenton, MI (US)

(73) Assignee: GII Acquisition, LLC, Davisburg, MI (US)

( * ) Notice: Subject to any disclaimer, the term of this patent is extended or adjusted under 35 U.S.C. 154(b) by 0 days.

(21) Appl. No.: 11/786,973

(22) Filed: Apr. 13, 2007

(51) Int. Cl.
*G06K 9/00* (2006.01)

(52) U.S. Cl. ............... 702/185; 324/237; 385/154; 356/241.1; 356/398

(58) Field of Classification Search ........... 702/185; 324/237, 240, 243; 348/92; 438/14; 365/241.1; 382/154; 250/559.19, 559.2, 559.36; 356/398, 356/394, 241.1
See application file for complete search history.

(56) References Cited

U.S. PATENT DOCUMENTS

| | | | | |
|---|---|---|---|---|
| 3,813,174 | A * | 5/1974 | Nowak et al. | 356/241.1 |
| 3,902,811 | A * | 9/1975 | Altman et al. | 356/398 |
| 4,755,753 | A * | 7/1988 | Chern | 324/237 |
| 4,831,251 | A | 5/1989 | Hanna | |
| 4,831,741 | A * | 5/1989 | Sogoian | 33/502 |
| 4,923,066 | A | 5/1990 | Ophir et al. | |
| 5,383,021 | A | 1/1995 | Hanna | |
| 5,568,263 | A | 10/1996 | Hanna | |
| 5,608,530 | A | 3/1997 | Gates | |
| 6,252,661 | B1 | 6/2001 | Hanna | |
| 6,285,034 | B1 | 9/2001 | Hanna | |
| 6,313,948 | B1 | 11/2001 | Hanna | |
| 6,501,554 | B1 * | 12/2002 | Hackney et al. | 356/601 |
| 6,522,777 | B1 * | 2/2003 | Paulsen et al. | 382/154 |
| 6,959,108 | B1 | 10/2005 | Bartelt et al. | |

(Continued)

FOREIGN PATENT DOCUMENTS

WO    WO 2005/022076 A2    3/2005

OTHER PUBLICATIONS

Military Standard, Visual Inspection Standard For Small Arms Ammunition Through Caliber .50, MIL-STD-636, Jun. 5, 1958, pp. I-III, 1-76.

*Primary Examiner*—Carol S Tsai
(74) *Attorney, Agent, or Firm*—Brooks Kushman P.C.

(57) ABSTRACT

A method and system are provided for inspecting manufactured parts such as cartridges and cartridge cases and sorting the inspected parts. The system includes an illumination assembly for evenly illuminating a plurality of annular, exterior side surfaces of a part when the part is located in a circumference vision station with rings of strobed radiation to generate corresponding reflected radiation signals. A plurality of imaging detectors in the form of CCD cameras are located at the vision station to generate a plurality of side images. The system further includes at least one side image processor for processing the side images of each part to identify parts having an unacceptable defect. The system further includes a mechanism for directing parts identified as having an unacceptable defect to a defective part area and directing parts not identified as having an unacceptable defect to an acceptable part area.

19 Claims, 13 Drawing Sheets

U.S. PATENT DOCUMENTS

| | | |
|---|---|---|
| 7,061,604 B1 * | 6/2006 | Beam et al. .............. 356/241.1 |
| 2005/0174567 A1 | 8/2005 | Hanna |
| 2006/0022669 A1 | 2/2006 | Nygaard |
| 2006/0236792 A1 | 10/2006 | Hanna |
| 2007/0117225 A1 * | 5/2007 | Capaldo et al. ............... 438/14 |

* cited by examiner

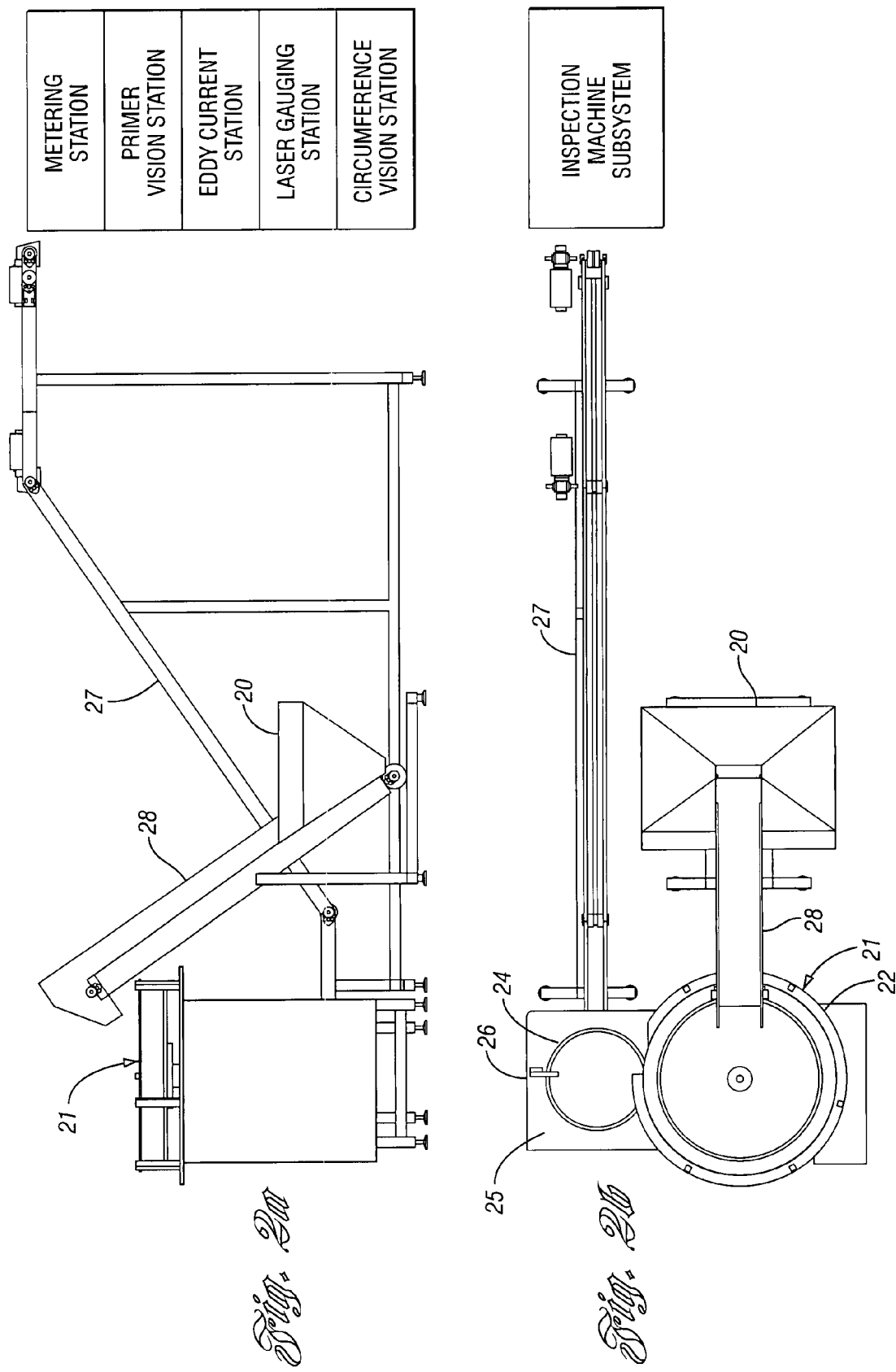

METHOD AND SYSTEM FOR INSPECTING MANUFACTURED PARTS AND SORTING THE INSPECTED PARTS

CROSS REFERENCE TO RELATED PATENT AND APPLICATIONS

This application relates to the following patent documents: U.S. Pat. No. 5,608,530; US 2006/0022669A2; and WO 2005/022076, all of which are owned by the assignee of this patent application.

BACKGROUND OF THE INVENTION

1. Field of the Invention

The present invention relates to methods and systems for inspecting manufactured parts such as cartridge cases and sorting the inspected parts based on the inspection.

2. Background Art

Inspection of defects on small arms ammunition cartridges and cases is a vital aspect in the manufacturing process, allowing for maintenance of a high level of quality and reliability in the munitions industry. Standards have been developed and applied by manufacturers for many years to assist in classifying various types of defects. Alternatively, a military standard is used such as that introduced in 1958 by the US Department of Defense, MIL-STD-636. For small arms ammunition calibers up to .50, this standard serves to evaluate and illustrate a practical majority of defects assembled as a result of extensive surveys covering all the small arms ammunition manufacturing facilities in the United States.

FIGS. 1a and 1b are side and bottom schematic views, respectively, of a .50 caliber case. As explained in the above-noted military standard, a case is to be counted as a defective because of a split case if the cartridge case shows a definite separation of the metal entirely through the case wall. A case is to be classified as either a "major" or "critical" defect depending on the location of split. A split in the (I), (S) or (J) position shall be counted as a "major" defect when no loss of powder occurs; and as a "critical" defect when loss of powder occurs. A split in the (K), (L) or (M) position shall be counted as a "critical" defect.

FIGS. 1c and 1d are side and bottom schematic views, respectively, of a .30 caliber case. As noted above, a case is to be counted as a defective because of a split case if the cartridge case shows a definite separation of the metal entirely through the case wall. A case is to be classified either as a "major" or "critical" defective depending on location of split. A split in the (I) or (J) position shall be counted as a "major" defect when no loss of powder occurs; and as a "critical" defect when loss of powder occurs. A split in the (K), (L), or (M) position shall be counted as a "critical" defect.

FIGS. 1e and 1f are side and bottom schematic views, respectively of a .45 caliber case. Again, as noted above, a case is to be counted as defective because of a split case if the cartridge case shows a definite separation of the metal entirely through the case wall. A case is to be classified either as a "major" or "critical" defective depending on the location of the split. A split in the (I) or (J) position shall be counted as a "major" defect when no loss of powder occurs; and as a "critical" defect when loss of powder occurs. A split in the (K), (L), or (M) position shall be counted as a "critical" defect.

U.S. Pat. No. 4,923,066 discloses an automatic visual inspection system for small arms ammunition which sorts visual surface flaws at high speed according to established standards which can be tailored to fit specific needs. The system employs techniques for performing inspection independently of human inspectors and allows for quick changeovers in the type of ammunition to which it is applied. The system comprises interface apparatus for receiving a supply of ammunition cartridges and providing each cartridge with a predetermined orientation, conveying apparatus for locating each of the cartridges for inspection in at least one inspection station, apparatus for imaging selected areas of each cartridge to provide video surface feature data associated therewith, and apparatus for processing the video surface feature data to detect the presence of a predetermined set of characteristics and provide output signals in accordance therewith, the conveying apparatus being operated to sort each of the inspected cartridges in accordance with the output signals. A preferred embodiment comprises four subsystems, a feeding subsystem, an imaging and handling subsystem, an operation subsystem, and a computers subsystem. The imaging and handling subsystem provides each cartridge with the necessary orientation for inspection by a video camera feeding video surface feature data to an image processing computer. The image processing computer makes a very high speed computation based on image processing techniques to decide whether the cartridges have manufacturing defects for sorting purposes. Since many surface flaws look the same in two dimensions such as scratches and splits or acid holes and stains, special lighting of the cartridges is used so that discrimination between them can be achieved on the basis of off-specular reflections.

U.S. Pat. No. 6,959,108 discloses an inspection system. Workpieces to be inspected are consecutively and automatically launched to pass unsupported through the field of view of a plurality of cameras. As a workpiece passes through the field of view of the cameras, a sensor is activated which communicates with a computer system to activate the cameras to capture an unobstructed image, or image data, of the workpiece. The image data is then analyzed by a computer program to verify whether the image data indicates that the workpiece does not meet established criteria and therefore is considered defective. If the image does not meet the established criteria, the workpiece is rejected and segregated from workpieces which have not been identified as defective.

U.S. Pat. No. 5,608,530 discloses a laser for producing a beam of radiation which is then refined in cross-sectional dimension by use of plano-cylindrical lenses. The refined beam of radiation falls incident on a part to be measured. The unobstructed portion of the beam is then bifurcated by a pair of reflective surfaces which produce non-parallel radiating beams; each beam comprised of the unobstructed portion of radiation which has passed radially opposed halves of the part. The magnitude of radiation present in each non-parallel radiating beam is then measured.

U.S. Pat. No. 4,831,251 discloses an optical device for discriminating threaded workpiece by the handedness by their screw thread profiles. The device present a pair of light beams which pass generally tangent to the workpiece at angularly displaced positions. The light beams are inclined to follow the helix direction of a given handedness of a workpiece. Upon axial advancement of a workpiece through the device, a chopped output from the photodetectors indicates that the handedness of the threads matches the inclination of the light beams. The oppositely threaded workpiece, however, provides a generally constant DC output. With appropriate signal processing electronics, an automatic system for discriminating workpieces by thread handedness is provided.

U.S. Pat. No. 5,383,021 discloses a non-contact inspection system capable of evaluating spatial form parameters of a workpiece to provide inspection of parts in production. The system causes parts to be sequentially loaded onto an inclined track where they pass through a test section. The test section includes a length detection array for measuring the length of the workpiece, which includes a source generating a sheet of light oriented in the longitudinal direction of the workpiece. The profile of the parts are evaluated by one or more light sources also creating a sheet of light oriented transversed to the longitudinal axis of the parts. Single channel photodetectors are provided for each of the sources which provides an analog output of the extent to which each sheet of light is occluded by the part. These outputs are analyzed through appropriate signal processing hardware and software to generate length and profile data related to the workpiece geometry.

U.S. Pat. No. 5,568,263 discloses a non-contact inspection system capable of evaluating spatial form parameters of a workpiece to provide inspection of parts in production. The system causes parts to be sequentially loaded onto an incline track where they pass through a test section. The test section includes a length detection array for measuring the length of the workpiece, which includes a source generating a sheet of light oriented in the longitudinal direction of the workpiece. The profile of the parts are evaluated by one or more light sources also creating a sheet of light oriented transverse to the longitudinal axis of the parts. First and second pairs of single channel photodetectors are provided for each of the light sources which provides a pair of analog outputs of the extent to which each sheet of light is occluded by the part, as well as an ability to eliminate noise or scintillation caused by a point source of light, for example with a laser light source. These outputs are analyzed through appropriate signal processing hardware and software to generate length and profile data related to the workpiece geometry.

U.S. Patent Application Publication No. 2005/0174567 discloses a system to determine the presence of cracks in parts. The presence of cracks is determined through the use of an imaging device and illumination source. The part is moved along a track where it is sensed by a position sensor to initiate the inspection. The illumination source projects a sheet of light onto the part to be inspected. The line formed by the intersection of the sheet of light and the part is focused onto the imaging device. The imaging device creates a digital image which is analyzed to determine if cracks are present on the part.

U.S. Patent Application Publication No. 2006/0236792 discloses an inspection station for a workpiece including a conveyor, a mechanism for rotating the workpiece, and a probe. The conveyor includes a fixture for locating the workpiece and the conveyor is configured to translate the workpiece in a linear manner. A mechanism, such as a belt, engages the workpiece thereby rotating the workpiece within the fixture. The probe is configured to indicate if the workpiece conforms to quality criteria. To facilitate inspection while the conveyor translates the workpiece, the probe is attached to a stage where the stage is configured to move the probe synchronously with the workpiece over an inspection region.

SUMMARY OF THE INVENTION

An object of the present invention is to provide a method and system for inspecting manufactured parts for a wider variety of defects than previously possible and sorting the inspected parts in an accurate, reliable and timely fashion based on the inspecting.

In carrying out the above object and other objects of the present invention, a method for inspecting manufactured parts and sorting the inspected parts is provided. The method includes consecutively conveying the parts so that the parts travel along a path which extends through a plurality of inspection stations including a circumference vision station. A plurality of annular, exterior side surfaces of a part are evenly illuminated when the part is located in the circumference vision station with rings of strobed radiation to generate corresponding reflected radiation signals. The reflected radiation signals are imaged to generate a plurality of side images. The side images of each part are processed to identify parts having an unacceptable defect. The parts identified as having an unacceptable defect are directed to a defective part area. The parts not identified as having an unacceptable defect are directed to an acceptable part area.

The rings of strobed radiation may have different angles of incidence with respect to their respective illuminated side surfaces.

The parts may include cartridge cases. A top surface of each case is located at a mouth end of the case and a bottom surface of each case is located at a primer end of the case.

The inspection stations may include a gauging station. The method may further include measuring one or more geometric dimensions of a part when the part is located in the gauging station, and processing the one or more geometric dimensions to identify parts having an unacceptable defect.

The inspection stations may include a mouth vision station. The method may further include generating a top image of each case located at the mouth vision station, and processing the top image to determine at least one of a split, a fold, an out-of-round condition, inner diameter and outer diameters and a dent located at the mouth end of each case.

The side images may be processed during the step of processing to determine at least one of a dent, a split, a perforation, a crack, a scratch, a wrinkle, a buckle, a bulge and a surface blemish located at the side surfaces of the case.

The inspection stations may include a primer vision station. The method may further include generating a bottom image of each case located at the primer vision station, and may include processing the bottom image to determine at least one of a split, a crack, flash-hole presence, primer absence, a cocked primer, primer pocket diameter and an inverted primer located at the primer end of each case.

Upon identification of a defective part, the defective part may be directed to a defective part area prior to conveying the defective part through any further inspection stations.

The unacceptable defect may include at least one of an external dent, a split, a crack and a surface blemish.

The parts may be conductive or semiconductive.

The inspection stations may include an eddy current station. The method may further include generating an electromagnetic signature of a part when the part is located in the eddy current station, and processing the signature to identify parts having an unacceptable defect.

Further in carrying out the above object and other objects of the present invention, a system for inspecting manufactured parts and sorting the inspected parts is provided. The system includes a conveyor subsystem and a feeder subsystem for feeding parts to the conveyor subsystem. The feeder subsystem and the conveyor subsystem consecutively conveys the parts so that the parts travel along a path which extends through a plurality of inspection stations including a circumference vision station. The system further includes an illumination assembly for evenly illuminating a plurality of annular, exterior side surfaces of a part when the part is located in the vision station with rings of strobed radiation to generate corresponding reflected radiation signals. A plurality of imaging detectors are located at the vision station, each of the detectors having an image plane for imaging the reflected radiation signals to generate a plurality of side images. The system further includes at least one side image processor for processing the side images of each part to identify parts having an unacceptable defect. The system further includes a mechanism including a part sorter for directing parts identified as having an unacceptable defect to a defective part area and directing parts not identified as having an unacceptable defect to an acceptable part area. The system further includes a system controller coupled to each of the inspection stations, the illumination assembly and the part sorter for controlling the sorting based on the inspecting.

The illumination assembly may include a plurality of ringlights having central apertures sized and aligned to allow the parts to travel unsupported through the plurality of ringlights at the vision station. Each of the ringlights has an axis and each of ringlights emits radiation in the form of a cone of radiation having a vertex located on its respective axis to evenly illuminate the annular, exterior side surfaces of the part.

The parts may include cartridge cases. A top surface of each case may be located at a mouth end of the case and a bottom surface of each case may be located at a primer end of the case.

The system may be a small and medium caliber ammunition inspection and sorting system.

The inspection stations may include a gauging station. The system may further include a non-contact gauging subsystem for measuring at least one geometric dimension of a part when the part is located in the gauging station to obtain measurement signals. The system may further include a signal processor for processing the measurement signals to identify parts having an unacceptable defect.

The inspection stations may include a mouth vision station. The system may further include means including an imaging detector for generating a top image of each case located at the mouth vision station. The system may further include a top image processor for processing the top image to determine at least one of a split, a fold, an out-of-round condition, inner and outer diameters and a dent located at the mouth end of each case.

The side images may be processed by the at least one side image processor to determine at least one of a dent, a split, a perforation, a crack, a scratch, a wrinkle, a buckle, a bulge and a surface blemish located at the side surfaces of the case.

The inspection stations may include a primer vision station. The system may further include means including an imaging detector for generating a bottom image of each case located at the primer vision station. The system may further include a bottom image processor for processing the bottom image to determine at least one of a split, a crack, flash-hole presence, primer absence, a cocked primer, primer pocket diameter and an inverted primer located at the primer end of each case.

The system may further include an actuator coupled to the system controller. Upon identification of a defective part, the controller may control the actuator to direct the defective part to a defective part area prior to conveying of the defective part through any further inspection stations.

The unacceptable defect may include at least one of an external dent, a split, a crack and a surface blemish.

The parts may be at least conductive or semiconductive. The inspection stations may include an eddy current station. The system may further include an eddy current subsystem for generating an electromagnetic signature of a part when the part is located in the eddy current station. The system may further include a signature processor for processing the signature to identify parts having an unacceptable defect.

The above object and other objects, features, and advantages of the present invention are readily apparent from the following detailed description of the best mode for carrying out the invention when taken in connection with the accompanying drawings.

BRIEF DESCRIPTION OF THE DRAWINGS

FIG. 2a is a side schematic view of a system for inspecting manufactured parts and sorting the inspected parts, the system being constructed in accordance with an embodiment of the present invention, the system including a feeder subsystem and an inspection machine subsystem;

FIG. 2b is a top view of the system of FIG. 2a;

DETAILED DESCRIPTION OF THE PREFERRED EMBODIMENTS

In general, one embodiment of the method and system of the present invention inspects manufactured parts such as cartridges and cartridge cases illustrated in FIGS. 1a-1f and sorts the inspected parts. The system is a complete system designed for the inspection and sorting of small and medium caliber ammunition. However, the system is also suitable for other small, mass-produced manufactured parts where external dents, splits, and surface blemishes are of concern. The subsystems which may be used for part handling and delivery may vary widely from application to application depending on part size and shape as well as what inspections are being conducted. The subsystems ultimately chosen for part handling and delivery have little bearing, however, on the nature of the subsystems conducting the various inspections, including visual inspections.

Referring now to FIGS. 2a and 2b, the system accepts parts from an infeed hopper 20 at one end and automatically feeds, orients and conveys them through a number of inspecting or inspection stations as illustrated in FIG. 2a. At a high level, the system is comprised of two subsystems, a feeder subsystem and inspection machine subsystem as illustrated in FIG. 2b. Each subsystem features a modular design with several possible upgrades providing varying levels of inspection capability.

Parts to be sorted are initially loaded into the hopper 20 where they are elevated and dumped at a controlled rate by a conveyor 28 into a centrifugal feeder bowl 21 having a scalloped rim 22. The bowl 21 loads parts into the radially oriented scallops on the outer rim 22. Tooling around the rim 22 takes advantage of asymmetrical mass distribution to deflect improperly oriented parts back into the feeder bowl 21. In this way, every part which passes out of the feeder bowl 21 and down a drop tube (not shown) is oriented in the same direction. In the case of ammunition inspection, parts are oriented to be traveling primer end first.

Since there is no way to predetermine how many parts will load into the scalloped outer rim 22 of the feeder bowl 21 facing the proper direction, the drop tube between the feeder bowl 21 and a dial table 24 allows for part accumulation. Low and high part sensors (not shown) halt the feeder bowl 21 or the dial table 24 as appropriate in the event of extended periods of above or below average part quantities. The drop tube loads a mechanism in the form of a plunger (not shown) which injects parts one at a time into individual pockets in the outer diameter of a wheel on the dial table 24. In order to ensure the proper timing of each injection cycle, the plunger which pushes the parts into the pockets is mounted to a cam-follower which runs on a cam profile which is cut into the dial wheel.

Figure 1E:
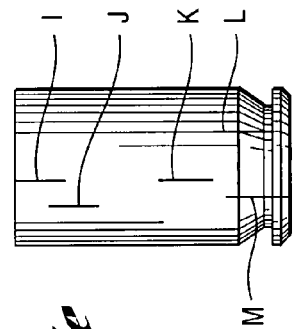
FIGS. 1e and 1f are side and bottom schematic views, respectively, of a .45 caliber cartridge case.
Figure 1F:
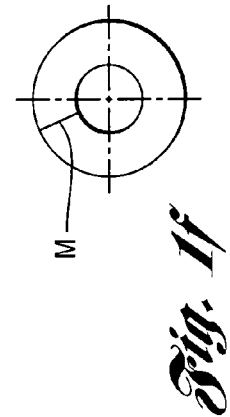
Figure 1C:
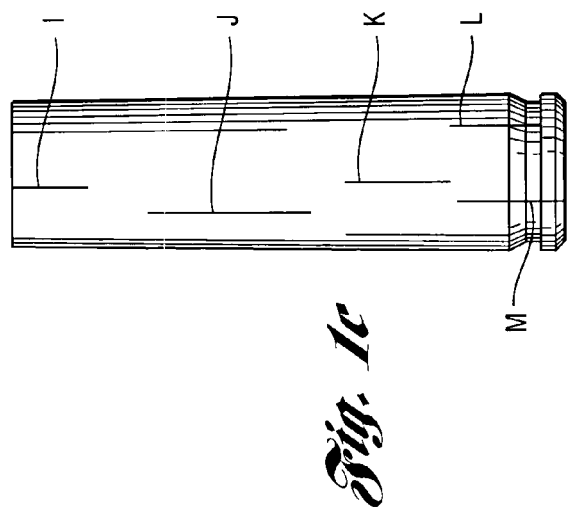
FIGS. 1c and 1d are side and bottom schematic views, respectively, of a .30 caliber cartridge case.
Figure 1D:
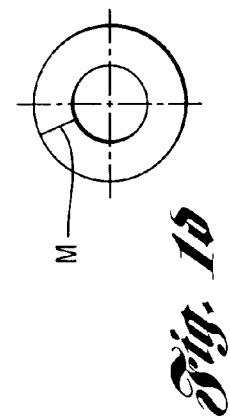
Figure 1A:
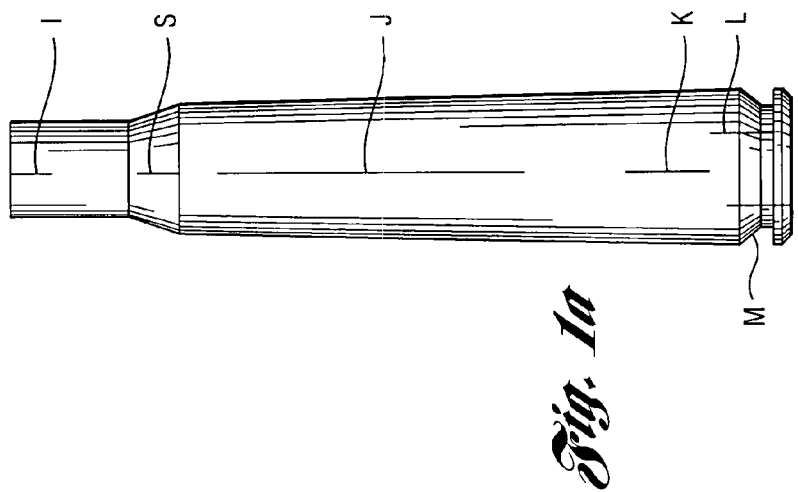
FIGS. 1a and 1b are side and bottom schematic views, respectively, of a .50 caliber cartridge case.
Figure 1B:
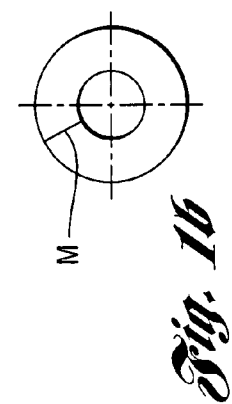
Figure 3:
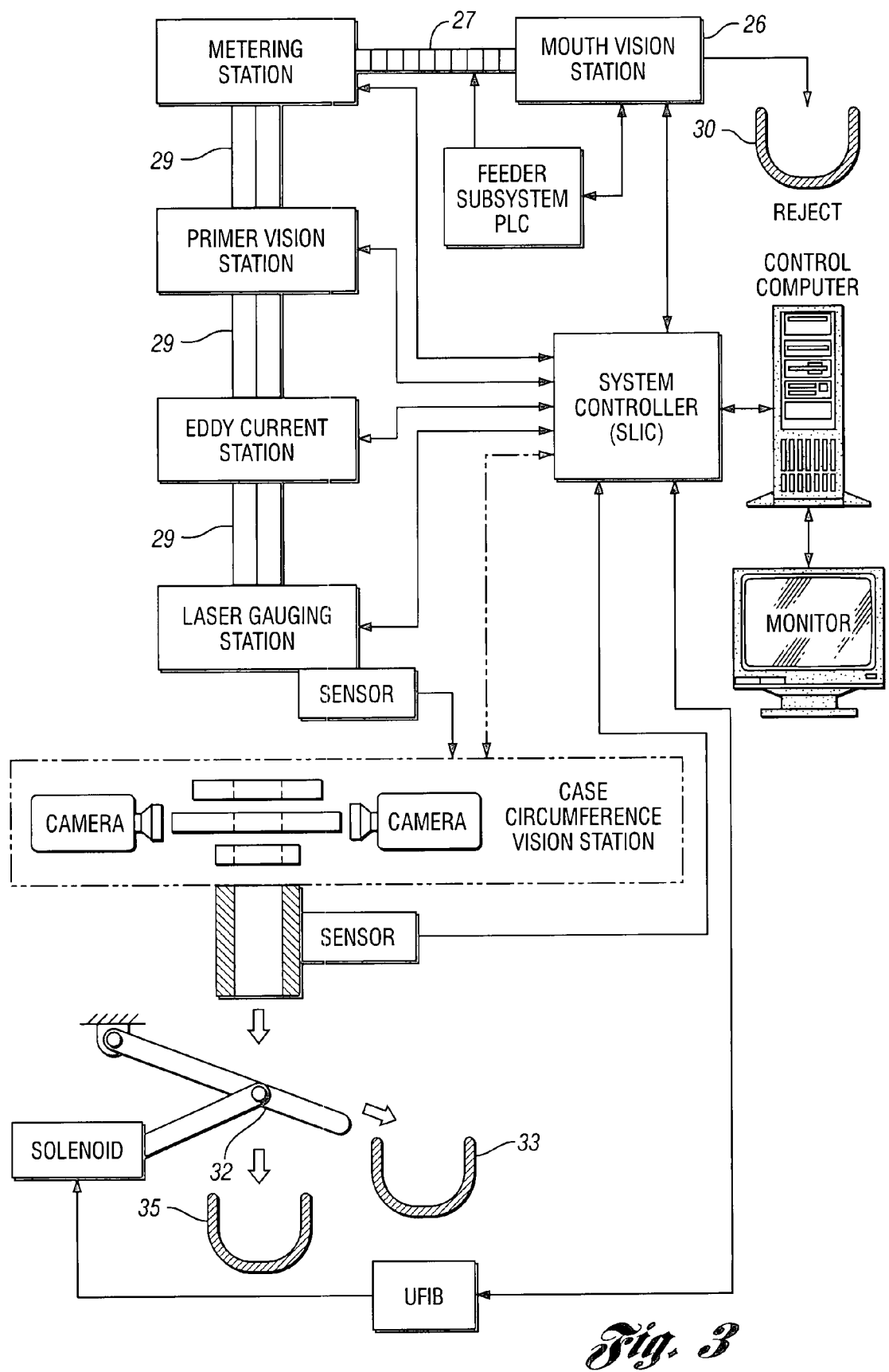
FIG. 3 is a schematic view illustrating various inspection stations and part conveying mechanisms and their control to inspect and sort the inspected parts.

As the parts traverse their circular course around the dial table 24, they are inspected from above with an on-axis CCD camera 25 at a top or mouth vision station 26 for cracks, out-of-roundness, inner and outer diameter measurements and splits on their top surface. In the case of ammunition inspection, the camera 25 detect splits, folds and dents in the case mouth of a cartridge case 31 (i.e., FIG. 4) which is illuminated by an LED light source. The camera 25 is calibrated to measure inner and outer diameters. Any parts which fail this inspection are rejected by an air blow-off actuator (not shown) into a reject area 30 as shown in FIG. 3. Parts passing the top-vision inspection are then shunted off the dial wheel and onto a conveyor 27 which raises them to the level of a V-shaped track input on the inspection machine subsystem. Immediately before they enter the V-shaped track 29 (i.e., FIG. 3), a metering station ensures parts are being delivered into the inspection machine subsystem at the proper rate with the required interval.

As previously mentioned, parts are provided to the inspection machine subsystem by the feeder subsystem at controlled regular intervals. The inspection machine subsystem includes several inspection stations as shown in FIGS. 2a and 3 located along the track 29 which may take the form of an AMPCO 18 bronze or 304 stainless steel vee-track oriented at a 35 degree angle. As the parts slide down the track 29, they pass through the inspection stations and are inspected one at a time. Parts which pass each of the inspections are actively accepted by a part diverter or flipper 32 located at the bottom of the track 29. The inspection stations located in the inspection machine subsystem may include one or more of the following modular inspection stations: bottom or primer vision, eddy current, laser gauging, and multi-camera circumference vision.

The bottom vision camera 34 (i.e., FIG. 4) is oriented slightly off-axis in order to avoid collision with the part as it slides down the track 29 bottom first. This station provides identical inspection capabilities to the top vision station 26 on the dial wheel discussed above. In the case of ammunition inspection, the camera 34 measures primer pocket diameter and looks for splits and cracks on the head of the case 31 (i.e., FIG. 4). Unprimed parts can be inspected for flash-hole presence. Primed parts with cocked or inverted primers will also be detected here.

The inspection machine subsystem can be configured with either one of two laser heads within the laser gauging station. The first laser head uses a single split-beam laser as described hereinbelow with reference to FIGS. 6 and 7 to measure a diameter profile at 125 kHz. A total of eight additional lasers spaced at 1" increments along the vee-track 29 measure the velocity of the part in vicinity of the laser head. Knowledge of the velocity of the part as it passes through the laser head, combined with accurate time-stamped diameter measurements allows the construction of a complete part profile.

The second laser head functions substantially identically to the first laser head with the exception that four split beam lasers are used to generate four linked diameter profiles. This significantly reduces the chance that an out-of-tolerance diameter will not be detected by occurring in the shadow of a laser profile. Additionally, the combination of the four complete part profiles can be combined to generate an approximate three dimensional part shape which can be used to extract part bend and eccentricity information.

Figure 6:
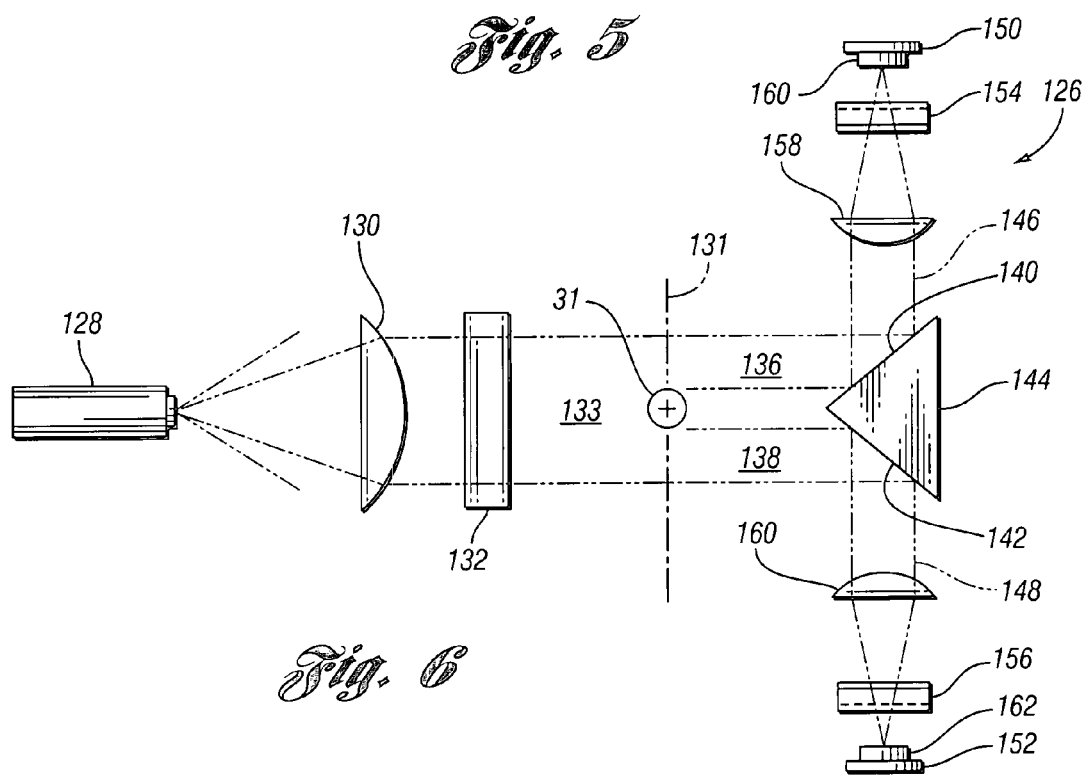
FIG. 6 is a side schematic view of one embodiment of an optical subsystem of the system of the present invention.
Figure 9:
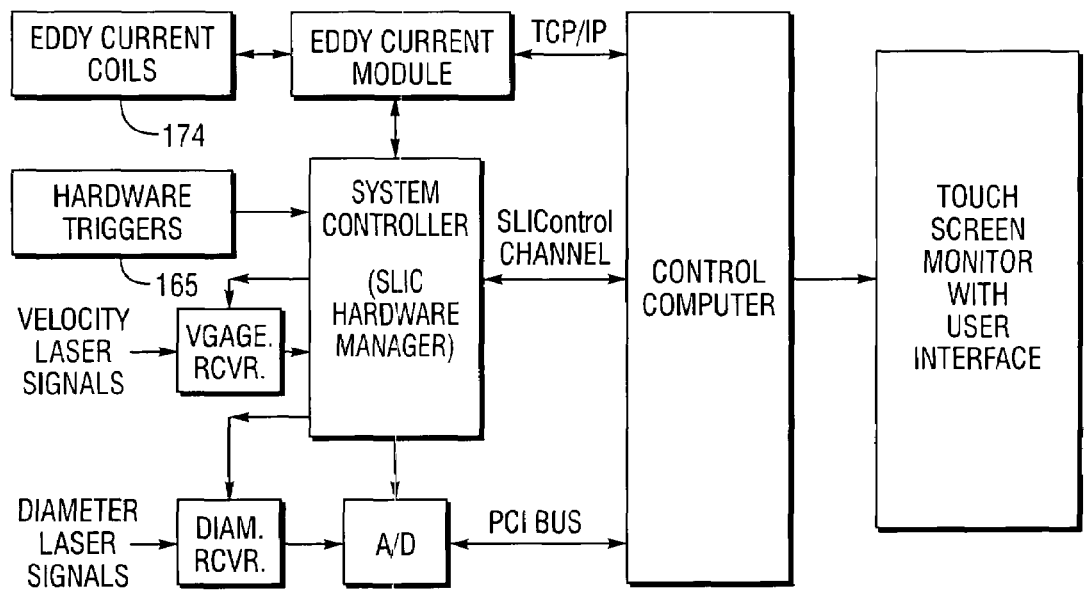
FIG. 9 is a more detailed block diagram of the hardware of FIG. 8.

Referring now to FIG. 6, one embodiment of an optical subsystem, generally indicated at 126, contained within the laser gauging station is now described. Generally, the subsystem 126 includes a laser 128 for producing a beam of radiation which is then shaped in cross-sectional dimension by use of plano-cylindrical lenses 130 and 132. The lens 132 focuses the beam 133 to a focal point which forms a line 131. The refined beam 133 of radiation falls incident on a part 31 to be measured. The unobstructed portions 136 and 138 of the beam 133 are then redirected by a pair of reflective surfaces 140 and 142 of a prism 144 producing radiating beams 146 and 148; each beam 146 and 148 comprises the unobstructed portion of radiation which has passed radially opposed halves of the part 31. The magnitude of radiation present in each radiating beam 146 and 148 is then measured by optical measurement sensors or optical or photo detectors 150 and 152 after passing through plano-cylindrical lenses 154 and 156, respectively, and negative concave lenses 158 and 160, respectively. The magnitude of radiation measured at sensing elements 160 and 162 of the detectors 150 and 152, respectively, is proportional to a dimensional measurement of the part 31. The diameter at each point on the part 31 along its direction of travel is measured. The photo detectors 150 and 152 provide diameter laser signals as shown in FIG. 9. The optical system 126 is described in greater detail in U.S. Pat. No. 5,608,530 noted above.

Preferably, instead of the prism 144, a pair of offset mirror elements may provide a pair of reflective surfaces to direct the beams 146 and 148 side-by-side to a pair of side-by-side photo detectors.

Figure 7:
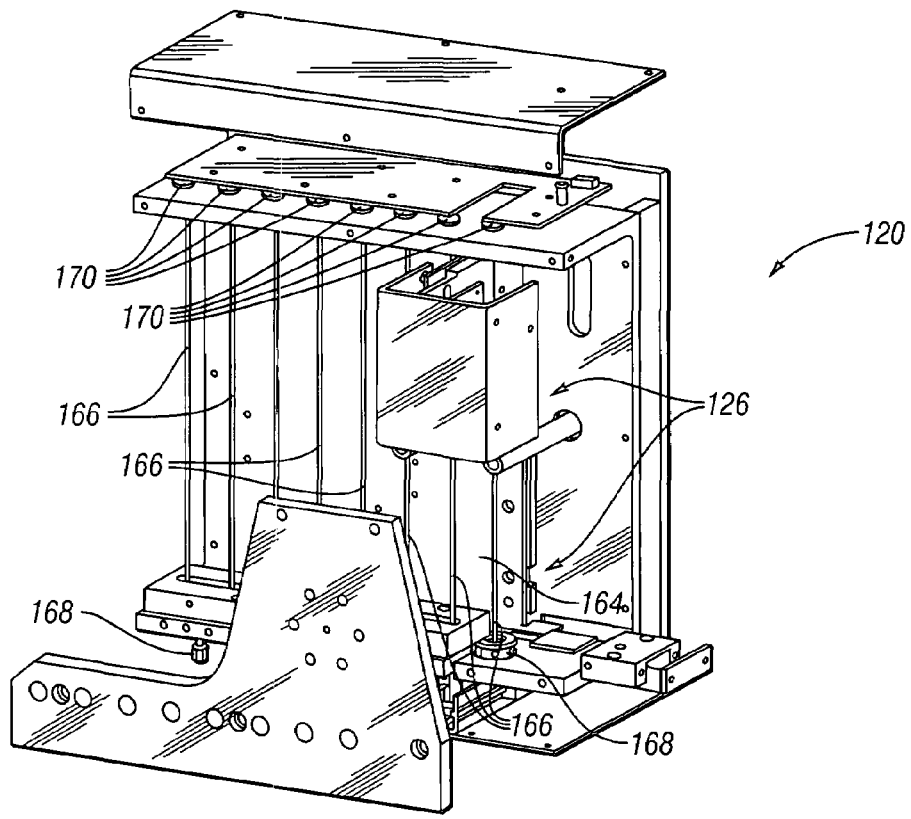
FIG. 7 is an exploded perspective schematic view of a portion of a system constructed in accordance with an embodiment of the present invention and illustrating the optical part measurement sensors and a trigger which generate corresponding electrical signals which are subsequently processed.

Referring to FIG. 7, the preferred optical subsystem 126 of FIG. 6 is incorporated in upper and lower portions of the system 120 to generate a sheet 164 of light through which a part 31 (not shown in FIG. 7) translated or conveyed by means of the inclined track 29 (not shown in FIG. 7) of the feed mechanism. The sheet 164 of light is generated in response to a trigger signal or pulse emitted by a central unit or hardware trigger 165 (i.e., FIG. 9) when a pencil light beam (not shown) in the track 29 is blocked.

Also shown in FIG. 7 are a series of eight parallel beams of light 166 which are generated by laser diode assemblies (only two of which is shown at 168) at predetermined spaced positions below the path taken by the translating part 134 along the track 29 so that the translating part 31 sequentially obstructs each of the series of beams. The beams 166 extend through a 0.06" gap formed between two halves of the track 29 and strike a corresponding series of spaced photo detectors 170 supported at an upper portion of the system 120. In this way, a velocity of translating part 31 is estimated based on the time at which the beams 166 are either detected or not detected by the photo detectors 170 as indicated by the velocity laser signals in FIG. 9 which are received by a velocity gauge receiver and subsequently processed. Typically, once the velocity of the translating part 31 is determined, the velocity is processed with the diameter laser signals to obtain a profile and features of the part 31 as will be described in greater detail hereinbelow.

The laser gauging subsystem software measures lengths and diameters in regions of interest on the part. Lengths are measured between user-defined "anchors." These anchors are picked out by dragging a box around an area of the on-screen profile and then selecting one of several edge detection tools. Another option is to create an anchor at a defined diameter on a taper. For example, an anchor may be created at the point wherein the part diameter equals 0.800 inches on the taper.

Rising edge, falling edge, midpoint and line intersection are available options. The software then looks for the selected edge type in the defined profile area and stores the identified location as an anchor. In this manner, any number of profile features can be picked out and defined as anchors. Once a collection of anchors have been created, internal lengths can be measured between them.

Diameters are measured by dragging a box around an area of interest within the on-screen profile. The user can then select whether they want to measure the maximum, minimum or average diameter in the selected region.

Tapers are measured in a fashion similar to diameters. The user defines an area of interest by dragging a box within the on-screen profile. The software then measures the taper angle inside this region.

During sorting, the user can define allowable tolerances for each constructed measurement. The software then keeps track of collected data for each part and displays not only the current part's measured dimensions, but also maximum, minimum, median and limited statistical distribution information for each measurement over the duration of the sorting process.

Figure 5:
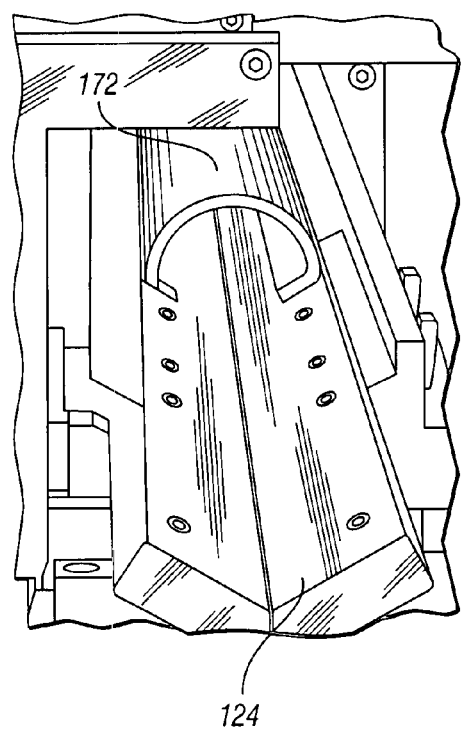
FIG. 5 is a perspective schematic view, partially broken away, of a part feed mechanism supported within a system constructed in accordance with an embodiment of the present invention wherein the system includes an eddy current sensor including eddy current coils.

The eddy current station of FIG. 3 includes an eddy current sensor 172 (FIG. 5) which generates an electromagnetic signature of the part and compares it with a saved "good" part profile. This comparative test can be tuned to detect the presence or absence of an anneal operation or missing bulk features. The eddy current sensor 172 which includes coils 174 (i.e., FIG. 9) which not only induce an eddy current in the translating part 31, but also sense the induced eddy current to provide a signal to an eddy current module (i.e., FIG. 9), which represents the amount of induced eddy current.

Again, pencil light beams in the V-slide monitor the part's progress as it falls down the inclined, upper surface 124 of the track 29 or slide. Each pencil light beam is associated with a small control unit or hardware trigger that produces an electrical pulse when the light is blocked; the pulse is referred to as a "trigger." Two of these are typically associated with the eddy current hardware. For eddy current, these essentially provide a "get ready", then a "get set" signal to the hardware than controls the induced eddy current. The eddy current subsystem is typically a commercially available subsystem.

The software for the eddy current subsystem displays the electromagnetic signature of a part on the complex impedance plane. The software is a purely comparative tool, generating no quantitative data. Several coil sizes are available including 2", 1.5" and 1". Additionally, coil frequency, AC gain and DC gain can be adjusted to generate a signature plot which is as large as possible without saturating the sensor 172.

Figure 8:
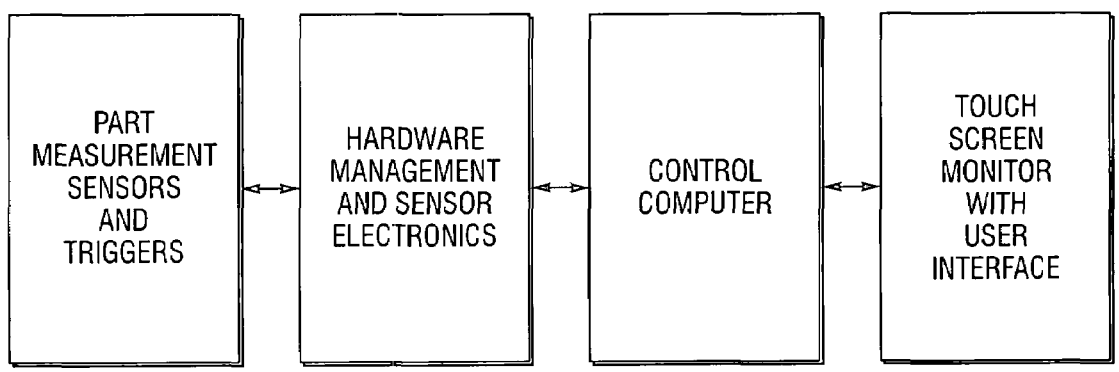
FIG. 8 is a generalized block diagram of hardware constructed in accordance with one embodiment of the system of the present invention.

Once the appropriate sensor settings have been determined, both good and bad parts are run to observe trends on the screen (i.e., FIGS. 8 and 9). The user can then define regions on the plot and establish logical rules to define good and bad parts based on their pattern observations. For example, a user might define a rectangular region and establish a rule such that IF a given part profile enters the associated rectangle, THEN flag the part as "good."

Referring again to FIGS. 8 and 9, the hardware for the eddy current and laser gauging stations of the system includes four main subsystems. Part measurement sensors and triggers include velocity gauge lasers and sensors, diameter gauge lasers and sensors, hardware triggers that monitor the passage of the part down the V-slide 29, and eddy current measurement coils 174. Hardware management and sensor electronics include a system controller in the form of a SLIC hardware manager and a number of modules required to convert the measurement signals to information a control computer can utilize. The control computer performs signal processing and manages the user interface at a monitor or monitor display.

Figure 10:
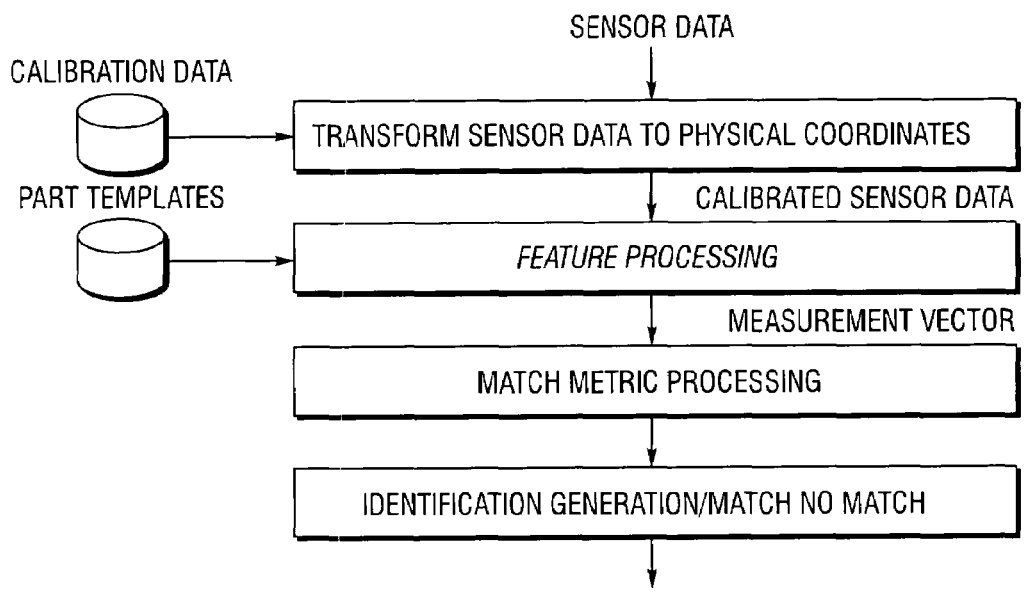
FIG. 10 is a block diagram which illustrates the flow of data utilizing one embodiment of a method of the present invention.

Referring now to FIG. 10, the data and signal processing system described therein illustrates how the system processes sensor data and identifies a part presented to the system. Using calibration data, sensor data is transformed to a description of the outline of the part, specified in calibrated physical coordinates. Feature processing extracts values for each feature contained in the entire part template data set. Match metric processing identifies the best match to the sensor data among the part templates. Identification generation evaluates the best match; if the match is good enough, the part is said to be identified, otherwise the part is not identified.

In general, when setting up a new part, the user chooses "features" of the part to be measured. The types of features include total length, internal length, diameter, thread, taper, and eddy current signature. For most features, the user chooses a region of the part where the measurement will be made, a nominal value of the measurement, and plus and minus tolerances. For some features, such as total length and eddy, the measurement region is the whole part. Also, for eddy current the user chooses a rectangle on the eddy screen of a display instead of a nominal value and tolerances. If the eddy signature hits the rectangle, then the part is good.

More particularly, in creating a template a gold or master part with known good dimensions is dropped on the inclined track so it slides down the track after the particular part is named. After the part has traveled the length of the track, an image of the part is displayed on a screen.

After a good image of the part is obtained, features are added to the template as previously mentioned. For example, when adding an internal length, points are determined on the part where one wishes to measure the internal length. One can add multiple internal lengths for each part. Internal lengths can be used to measure features like: shoulder length, head height, under the head to the start of a part, and any length measurement needed inside of a part.

Such predefined points are also useful for other template features like diameters and tapers. Such predefined points are useful when looking for rising and falling edges of the part as well as when looking for minimum and maximum diameters of the part.

The diameter feature is used to measure diameters around a part. Multiple diameters can be added for each part. One can select minimum and maximum diameters for a selected area (or a small groove within a selected area) or one can average all the diameters in the area selected.

With respect to taper features, tapers are used to measure tapered angles on a part. Multiple tapers can be added for each part.

The external/overall length feature is automatically added to the list of features once the part has been scanned (i.e., travels down the track). The length is measured by the velocity sensors and is determined by the start and end predefined points.

With respect to eddy current, a frequency parameter is initially set up for a particular part. A relatively low frequency such as 1 KHz may be used to check for material and a relatively high frequency such as 50 KHz may be used to check for plating of a part. During the generation of a template for eddy current, a known good part is sent down the track to get a signature of the part on the screen. After obtaining a signature, one may have to adjust the parameters of the frequencies and the gains while testing a good part, until a good image is obtained on a screen of a display. A good image should have a defined area, like a loop, that will have some space inside it. Alter establishing the eddy current signature of a good part, the area of the signature one wants to inspect may be highlighted.

Figure 4:
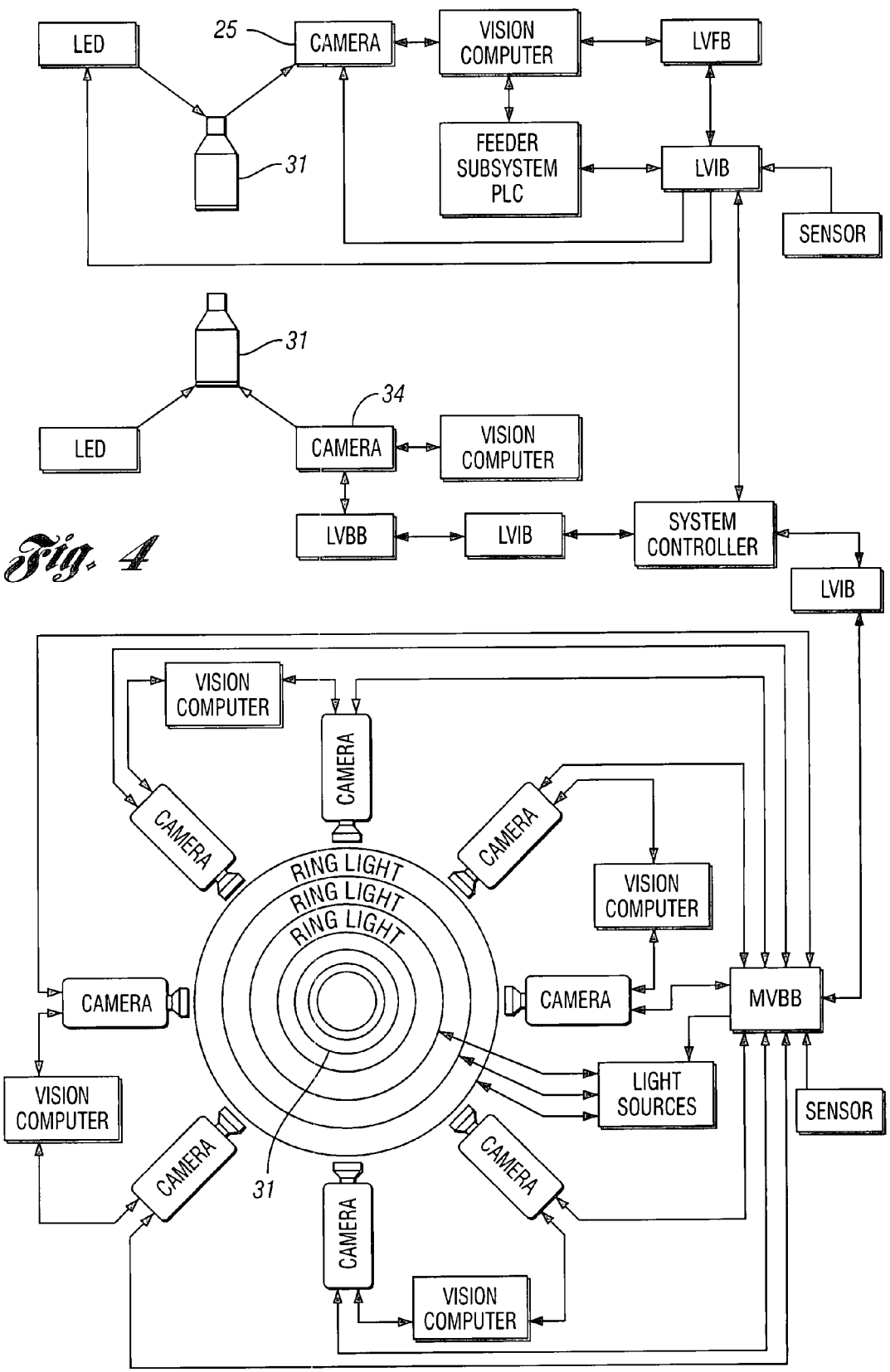
FIG. 4 is a detailed schematic view of hardware located at top, bottom, and circumference vision stations of the inspection stations and their control.

After passing through the laser gauging station, a light curtain sensor verifies the passage of the part, the track 29 ends and the part 31 falls freely for about 3.75 inches. While unconfined and unobstructed, the part is imaged by eight CCD cameras or image detectors located around the circumference of the part 31 at 45 degree intervals as indicated in FIG. 4. Software locates and defines several regions of interest on the part 31 and inspects those regions using any number of customizable tools for user defined defects. In order to allow the system to be able to locate and recognize a wider variety of defects, a plurality of adjustable, xenon strobe ringlights illuminates annular portions of the exterior side surfaces of the part from a variety of angles.

The parts 31 are then caught in a 1.5" diameter clear tube 37. A light curtain sensor verifies that the parts completed the jump and were collected successfully. The solenoid-actuated flipper 32 at the bottom of the tube 37 actively accepts those parts which have passed every one of the above tests. This flipper 32 rests by default in the reject position so that parts will not be falsely accepted in the unlikely event of a hardware or software malfunction.

The strobed xenon ringlights are fully adjustable to provide even illumination around the circumference of the part. The system accommodates lights of several sizes. By varying the size of the strobed lights as well as their axial locations, desired light incidence angles can be established which will provide proper illumination to detect defects of interest. Reflected light is received by a ring of eight inward-pointing CCD cameras mounted on a ring around the circumference of the part (i.e., FIG. 4).

While the vision system is partially described hereinbelow, a more complete description of the vision system can be found in Appendix A hereto.

The detection of dents relies on the alteration of the angle of reflected light caused by a surface deformation on the inspected part. Light which is incident on a surface dent will reflect along a different axis than light which is incident on a non-deformed section of circumference.

There are generally two ways to detect dents using this method. One way is to orient the light source so that light reflected off the part exterior is aimed directly into a camera aperture. Light which reflects off a dented region will not reflect into the camera and will appear as a dark spot on the otherwise bright background.

In the second way, the light source is positioned with a shallower angle to the part. This will result in a low background illumination level with dents appearing as well defined bright spots on the image.

Figure 11:
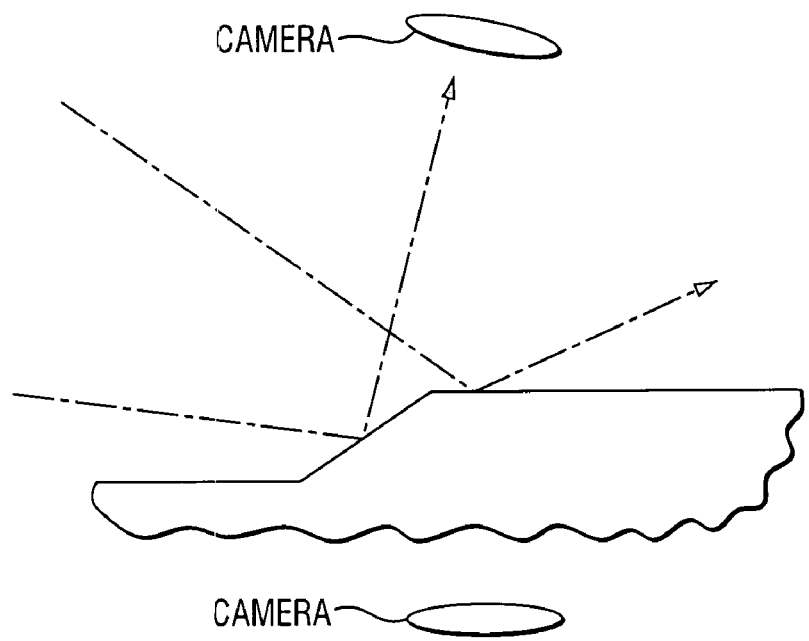
FIG. 11 is a schematic view illustrating light rays emitted from ringlights of various diameters used to illuminate tapered regions on a part; this results in tapered sections appearing with bright backgrounds while flatter regions show up with dim backgrounds.

The circumference vision subsystem may rely on a combination of the above-noted ways to detect dents on parts with multiple tapered sections as illustrated in FIG. 11. Recent data appears to suggest that a dim background works best under some circumstances.

Figure 12:
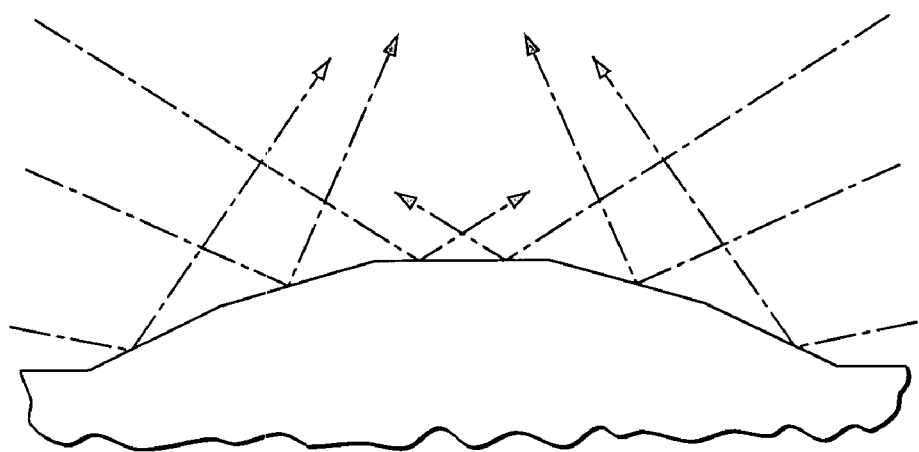
FIG. 12 is a schematic view illustrating light rays emitted from six ringlights thereby allowing parts to be inspected with up to two tapers at each end of the part.

Preferably, the vision subsystem has three tiers of lights, each of which can be independently adjusted back and forth in order to properly illuminate a given taper. Furthermore, a second set of three lights is located to illuminate tapers which might occur on the other end of the part. FIG. 12 depicts a part which takes advantage of all six of the available lights.

Because the part is in freefall when the images are acquired, the software must auto-locate the part and identify regions of interest using preset visual clues. These regions can be adjusted in size and shape to best fit the part being tested. In the case of ammunition inspection, these regions include the head, extractor groove, case, shoulder taper, and mouth.

Defect detection in each region is conducted by first running several image processing algorithms and then analyzing the resultant pixel brightness values. Groups of pixels whose brightness values exceed a preset threshold are flagged as a "bright defect," while groups of pixels whose brightness values lie below a preset threshold are flagged as a "dark defect." Different image processing techniques and threshold values are often needed to inspect for bright and dark defects, even within the same part region.

Top and Bottom Vision Station Software

The vision software for these two subsystems is identical on account of the similarity of function. Because parts to be inspected are generally cylindrical at least in part, inspections in this software are conducted within regions outlined by user defined circles. These circles can be generated in several ways. The simplest is to define a circle diameter and center it on a particular pixel within the display. This has the obvious side effect of being sensitive to motion from part to part within the field of view. Careful attention to part stability and triggering can mitigate this concern considerably.

Alternatively, the user can define a large circular region (using the method above) and instruct the software to search for a circular part feature within the region. This allows the user to pick out an outer or inner diameter, a chamfer edge, or a scribed ring, etc.

Once a set of circles has been defined, inspections can be set up between these circles. Bright or dark defects can be searched for (as discussed below under Circumference Vision), and diameter measurements can be conducted. The thickness of a wall section can be calculated using measurements from an inner and outer diameter. The imprints of a head-stamp can be detected as bright/dark defects allowing the presence of such a feature to be determined. Text recognition may be implemented.

System Logic

Referring to FIGS. 3 and 4, the core of the system logic is the System Logic Interface Controller (SLIC) or system controller. This controller takes "PART RESULT" and "PART COMPLETE" inputs from all of the inspection stations in the system. The SLIC communicates directly with a Uni-Flipper Interface Board (UFIB) and instructs the flipper 32 to actively accept parts into a part receive area 33 for which it has received positive part result and part complete signals from each inspection station. Each inspection station must have reported a positive part and part complete signal for the SLIC to instruct the UFIB to open the flipper 32 (as illustrated in FIG. 3) through a solenoid. Otherwise, the defective parts are directed to a defective part area 35.

Top Vision

Referring to FIG. 4, images taken by the top vision camera 25 located on the feeder dial table are processed by a dedicated vision computer. Once the vision computer has performed the user-defined tests and rendered a decision, it communicates via RS-232 cable to the Lorus Vision Feeder Breakout (LVFB) which in turn passes the signal onto the feeder subsystem PLC as well as the Lorus Vision Interface Board (LVIB). The LVIB then communicates part result and part complete to the system controller (SLIC) via Ethernet cable.

Bottom Vision

Images taken by the bottom vision camera 34 located on the vee-track 29 are processed by a dedicated vision computer. Once the vision computer has performed the user-defined tests and rendered a decision, it communicates back to the bottom vision camera 34 whether or not a defect was detected. The camera 34 then sends a digital IO signal to a Lorus Vision Breakout Board (LVBB) which then converts this signal and forwards it on to an LVIB. The LVIB then communicates part result and part complete to the system controller (SLIC) via Ethernet cable as indicated in FIG. 4.

Eddy Current

Incoming parts encounter a balance sensor which activates an eddy coil located in the base of the inspection machine subsystem. The signal from this balance coil is used to calibrate the eddy current subsystem. Shortly thereafter, the parts encounter the trigger sensor which activates data acquisition from the primary eddy coil. The eddy control board compares the calibrated eddy signal with a stored impedance profile and delivers part result and part complete signals to the system controller (SLIC) as indicated in FIG. 9.

Laser Gauging

As indicated in FIG. 9, as the part passes through the split beam diameter laser, the outputs of the laser detectors (either two or eight as previously described) are sampled by the main PC's A/D board at 125 kHz. This generates a matrix of time-stamped diameter data. As the parts pass the eight velocity lasers, the SLIC board captures the times associated with the rising and falling edges of the parts blocking each beam. When a part un-blocks the last velocity laser, the SLIC sends these time values to the digital I/O card on the main PC. The PC software uses the velocity laser timestamps to calculate the velocity of the part as it was passing through the split beam diameter laser. This velocity data is then combined with the recorded diameter data to generate an overall part profile.

The pre-defined tolerances are compared to the newly generated part profile and the software determines whether the part is good or bad. It then communicates part result and part complete signals to the SLIC via digital I/O.

APPENDIX A

Vision System for the Detection of Surface Defects on Small Manufactured Parts

This vision system is especially designed for the inspection and sorting of small and medium caliber ammunition. The system is also suitable to inspect other small, mass-produced, manufactured parts where external dents, splits, and surface blemishes are of concern.

System Design

The vision system is frequently installed as part of a larger inspection machine. Therefore, the methods for part handling and delivery might vary widely from application to application depending on part size and shape as well as what other inspections are being conducted. The methods ultimately chosen for part handling and delivery have little bearing however on the nature of the system conducting the various visual inspections.

The system being proposed includes a number of strobed xenon ring-lights which are mechanically adjustable to provide even illumination around the circumference of the part. The system accommodates lights of several sizes. By varying the size of the strobed light as well as its axial location, a desired light incidence angle can be established which will provide proper illumination to detect defects of interest. Reflected light is received by a ring of eight inward-pointing CCD cameras mounted on a frame around the circumference of the part.

Both the strobed lights and the eight cameras are controlled by a laser gate trigger. When an incoming part triggers the laser gate, a signal is sent to the Multi-Vision Breakout Board (MVBB) (i.e. FIG. 4) which, in turn, instructs the ring-light strobes to flash and the cameras to take pictures. Image data is fed via Firewire to dedicated rack-mount vision computers. Each computer is assigned to process the images generated from two cameras, meaning four vision computers are required to handle the image processing needs for the complete vision system. Each computer performs a series of user-defined inspections and then communicates back to its assigned cameras whether or not defects were detected in their respective images. The cameras then send digital IO signals to the MVBB which performs an OR logic operation on each of the signals it receives from the cameras. In this manner, if any of the cameras has detected a defect, an overall part defect signal is generated.

Lighting

It is desirable that the system be as flexible as possible regarding the variety of parts which it is capable of inspecting. Since the core of any good vision system is good lighting, it is therefore important that the lights be adjustable in order to properly illuminate as many part shapes and sizes as possible. Furthermore, many parts include regions with varying tapers and multiple diameters. It is therefore important to provide for multiple lights located at varying diameters, each dedicated to illuminating a particular feature.

Dent Detection

The detection of dents relies on the alteration of the angle of reflected light caused by a surface deformation on the inspected part. Light which is incident on a surface dent will reflect along a different axis than light which is incident on a non-deformed section of circumference.

There are generally two ways to detect dents using this theory. One option is to orient the light source so that light reflected off the part exterior is aimed directly into the camera aperture. Light which reflects off a dented region will not reflect into the camera and will appear as a dark spot on the otherwise bright background. This situation is depicted in FIG. 13.

Alternately, the light source can be positioned with a shallower angle to the part. This will result in a low background illumination level with dents appearing as well defined bright spots on the image. This concept is illustrated in FIG. 14.

Figure 13:
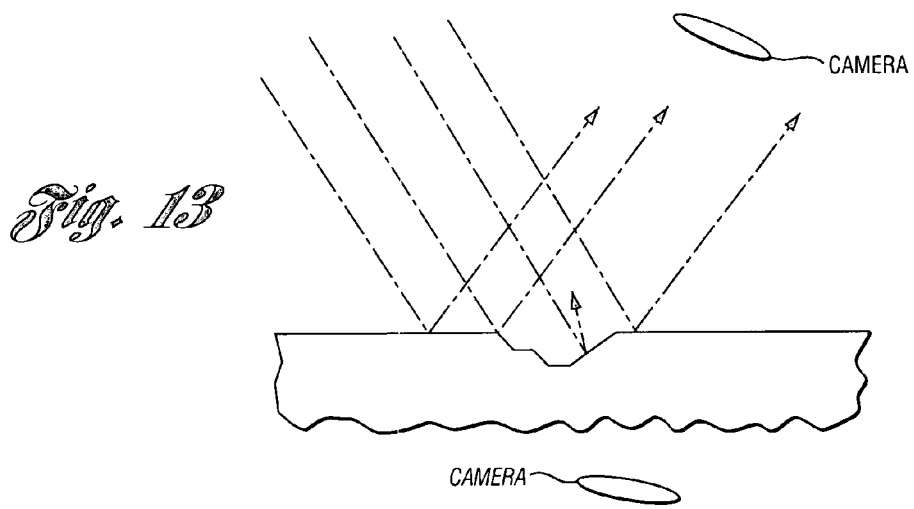
FIG. 13 is a schematic view illustrating light reflecting off the smooth surface of the part and directed into a camera, thereby registering as a bright background; light rays encountering a surface dent is reflected away, thereby creating a dark spot.
Figure 14:
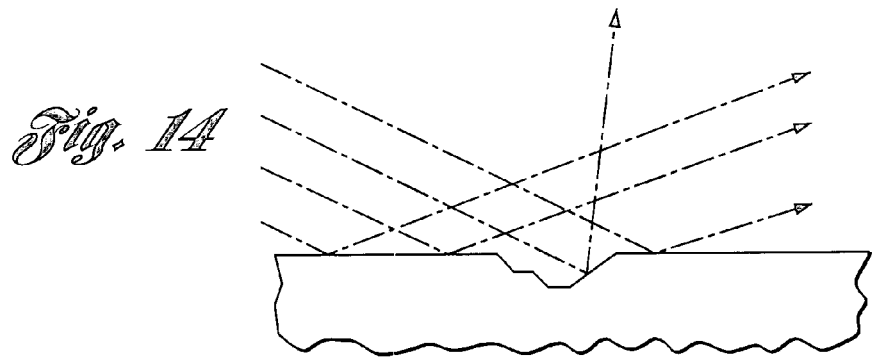
FIG. 14 is a schematic view similar to the view of FIG. 13 wherein the camera registers a dim background light level in response to a smooth and even surface; incident light rays which encounters a surface dent is detected as a bright spot in the recorded image.

The vision system relies on a combination of the concepts illustrated in FIG. 13 and FIG. 14 to detect dents on parts with multiple tapered sections. In particular, a bright background is created in highly tapered regions (with dents appearing as dark spots) while a dim background is created in flatter regions (with dents appearing as bright spots).

In fact, the vision system has three tiers of lights, each of which can be independently adjusted back and forth in order to properly illuminate a given taper. Furthermore, a second set of three lights is located to illuminate tapers which might occur on the other end of the part. FIG. 12 depicts a part which takes advantage of all six of the available lights.

Figure 15:
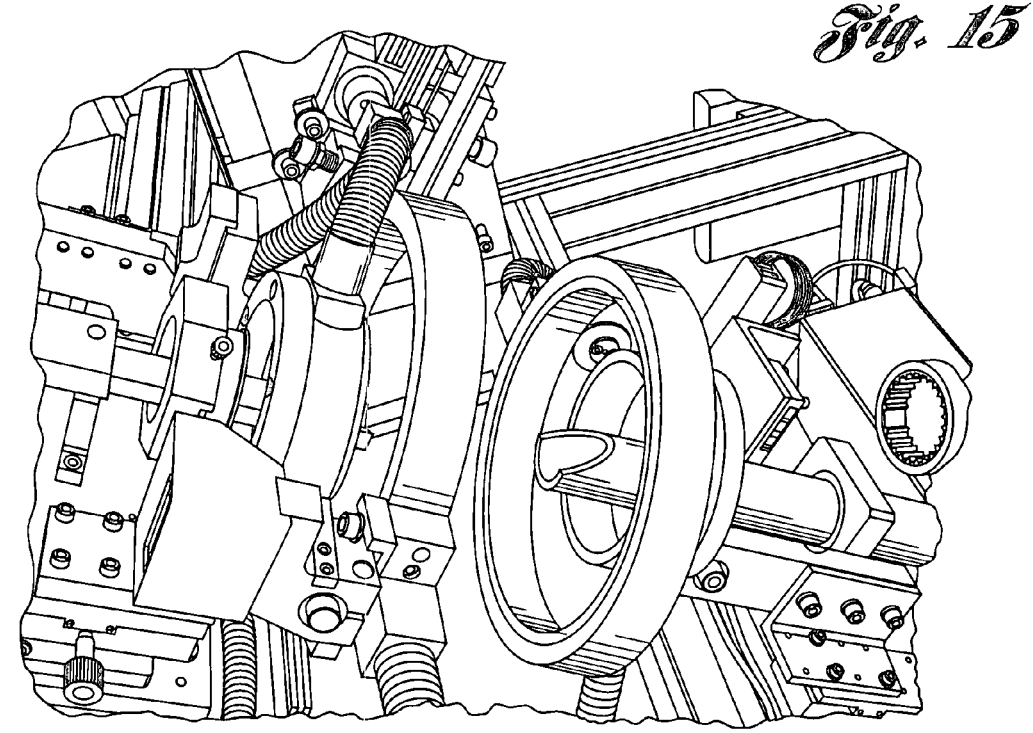
FIG. 15 is a schematic view of the ring lights used in the vision system of the embodiment of the invention; parts enter from the left on a bronze vee track, fall freely for a brief period while they're photographed by the eight cameras mounted around the circumference of the part, and are then caught in a clear acrylic tube; the ring lights used to illuminate various tapers can be seen on either side of the gap between the bronze vee track and the acrylic catch tube.

A schematic of this arrangement is shown in FIG. 15.

Perforation Detection

Detecting perforations uses both of the principles outlined above. The task is much simpler however, as the region containing the defect is completely non-reflective. Therefore, perforations are visible as dark spots on surfaces illuminated by either shallow or steep angle illumination.

Software

Because the part is in freefall when the images are acquired, the software must auto-locate the part and identify regions of interest using preset visual clues. These regions can be adjusted in size and shape to best fit the part being tested. In the case of ammunition inspection, these regions include the head, extractor taper, case, shoulder taper, and mouth.

Defect detection in each region is then conducted by first running several image processing algorithms and then analyzing the resultant pixel brightness values. Groups of pixels whose brightness values exceed a preset threshold are flagged as a "bright defect," while groups of pixels whose brightness values lie below a preset threshold are flagged as a "dark defect." Different image processing techniques and threshold values are often needed to inspect for bright and dark defects, even within the same part region.

Part Location

Locating the part in the image is accomplished by running a series of linear edge detection algorithms. This algorithm uses variable threshold, smoothing and size settings to determine the boundary between a light and dark region along a defined line. These three variables are not generally available to the user, but are hard-coded into the software, as the only time they will generally need to change is in the event of large scale lighting adjustments.

Figure 16:
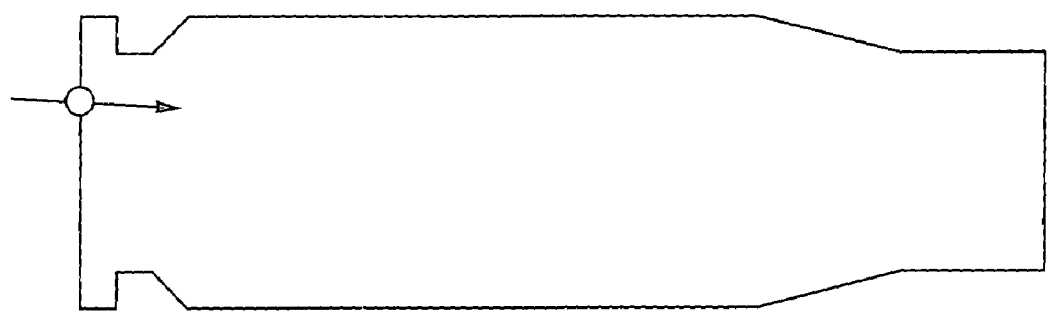
FIG. 16 is a schematic view of a part to be inspected within a rectangle wherein a linear edge detection algorithm traverses from left to right and locates the left hand edge of the part.

The software first uses the above edge detection algorithm to find the back (left) end of the part in the image as shown in FIG. 16.

Figure 17:
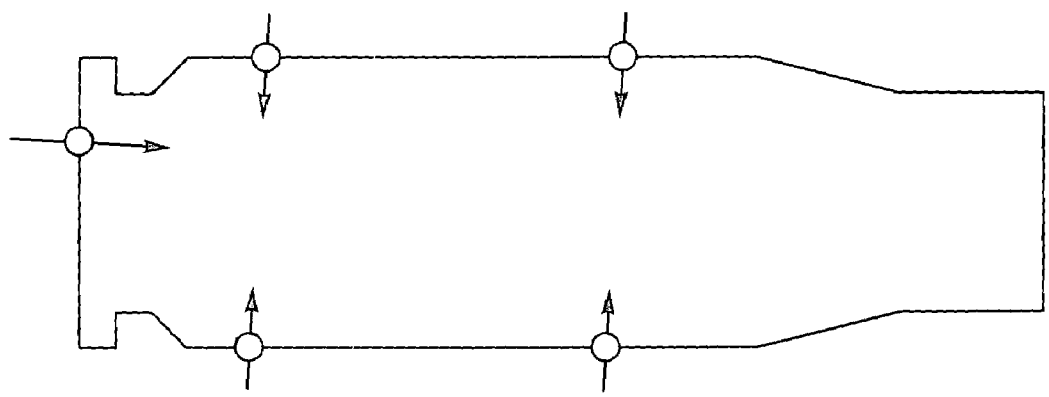
FIG. 17 is a schematic view similar to the view of FIG. 16 wherein four edge searches are performed to find the top and bottom edges of the part.

Once the left edge of the part has been located, the software runs four more edge searches along the top and bottom edges of the part as shown in FIG. 17.

Figure 18:
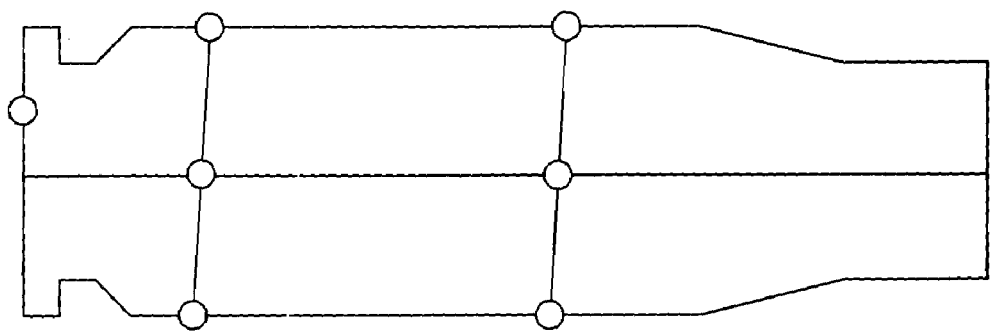
FIG. 18 is a schematic view similar to the views of FIGS. 16 and 18 wherein the midpoint between each top and bottom edge pair is located and used to find the overall part centerline.

Once the top and bottom edges of the part have been located, the midpoints of the edge pairs are calculated and joined in order to find the centerline. This is shown in FIG. 18.

Figure 19:
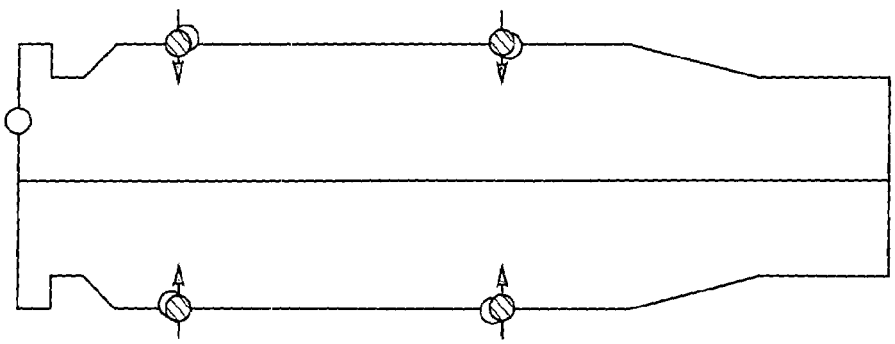
FIG. 19 is a schematic view similar to the views of FIGS. 16-18 wherein the linear edge detection algorithm is repeated along the top and bottom of the part, this time along a vector perpendicular to the centerline.

The centerline search is then performed again, but rather than conducting the linear edge detections in the vertical direction, they are conducted perpendicular to the newly found centerline. This iteration reduces the small angle error associated with any potential misalignment of the part in the field of view. This is shown in the darkened portions in FIG. 19.

A new centerline found using the results of the repeated top and bottom edge search.

Figure 20:
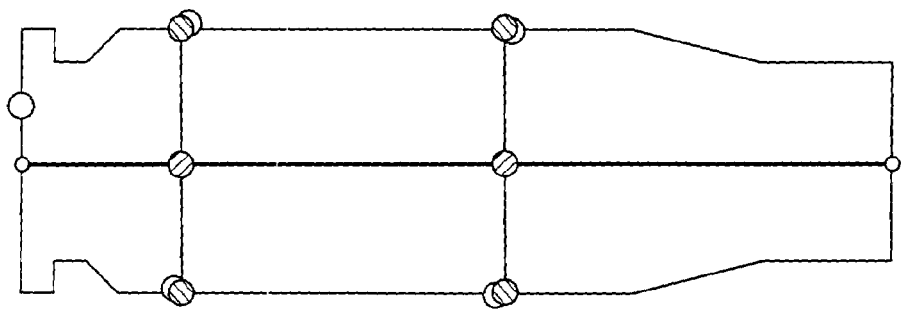
FIG. 20 is a schematic view similar to the views of FIGS. 16-19 wherein the centerline was found by connecting the midpoints of the segments defined by the new edge locations.
Figure 21:
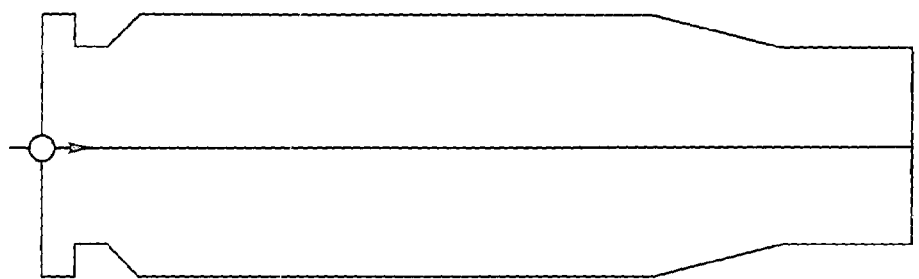
FIG. 21 is a schematic view similar to the views of FIGS. 16-20 wherein the left-hand edge is located again, this time along the centerline of the part.

Finally the left edge is again located, this time along the new centerline found in FIG. 20. This action locates the very center of the left-hand edge of the part as shown in FIG. 21.

Part Regions

Figure 22:
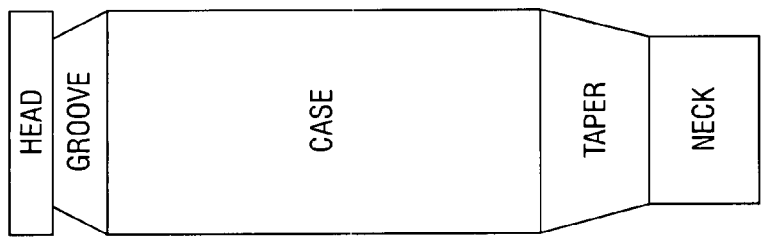
FIG. 22 is a schematic view similar to the views of FIGS. 16-21 wherein a framework in this figure is applied to the part once it has been located; each of the regions defined here can be resized in order to achieve the best fit for the part being inspected.

Once the part has been located in the image, a framework of part regions is defined using a hard-coded model of the anticipated part shape. In the case of ammunition, the regions defined by the framework include head, extractor groove, case, taper, and neck. Each of these regions can be varied in length and width through the user interface in order to adapt the software to varying case sizes. Note that although regions can be adjusted in size, they cannot have their bulk shape changed. A checkbox allows the taper and neck regions to be removed in order to inspect pistol cases (which do not have a taper). The size of the region framework as well as the state of the Taper/No-Taper checkbox is saved in the part profile. FIG. 22 shows the definition of the various regions on the part.

Figure 23:
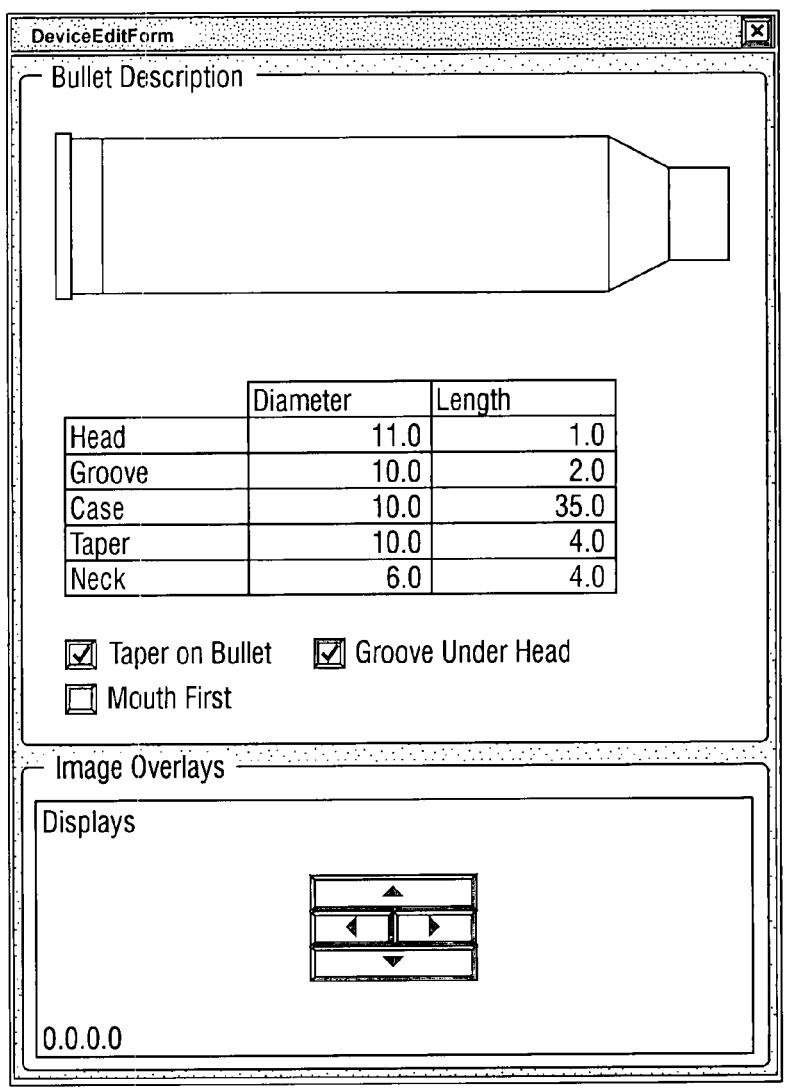
FIG. 23 is a schematic view of screenshot which describes a bullet to be inspected.

This region definition is shown in FIG. 23. Note how the diameter of the groove has been set to be the same as the diameter of the case, resulting in a rectangular groove profile, rather than the trapezoid that is more frequently used.

Defect Search

Figure 24:
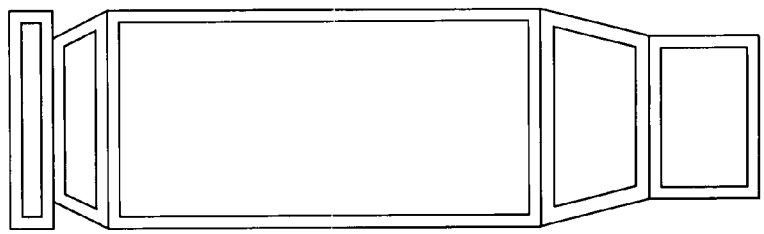
FIG. 24 is a schematic view similar to the views of FIGS. 16-22 wherein buffers are applied once the case regions have been defined; the various defect inspections will be applied only in the buffered areas; thereby reducing the chance that boundary artifacts will disrupt the integrity of the defect detection algorithms.

Once the case regions have been defined, a buffer distance is applied to the inside edges of each region. These buffered regions define the area within which the defect searches will be conducted. By buffering the inspection regions, edge anomalies and non-ideal lighting frequently found near the boundaries are ignored. The size of the buffers can be independently adjusted for each region as part of the standard user interface and is saved in the part profile. This concept is demonstrated in FIG. 24.

There are two general defect detection algorithms that can be conducted in each region. These two algorithms are closely tied to the detection of dents and perforations respectively as discussed above in the lighting section. More generally however, they correspond to the recognition of a group of dark pixels on a bright background or a group of bright pixels on a dark background.

Although there are only two defect detection algorithms used across all the regions on the part, the parameters associated with the algorithm can be modified from region to region. Additionally, the detection of dark and/or bright defects can be disabled for specific regions. This information is saved in the part profile.

Dark Defects

The detection of dark defects is a 6 step process.
1. Logarithm: Each, pixel brightness value (0-255) is replaced with the log of its brightness value. This serves to expand the brightness values of darker regions while compressing the values of brighter regions, thereby making it easier to find dark defects on a dim background.
2. Sobel Magnitude Operator: The Sobel Operator is the derivative of the image. Therefore the Sobel Magnitude is shown below:

$$S_M = \sqrt{\left(\frac{\partial f}{\partial x}\right)^2 + \left(\frac{\partial f}{\partial y}\right)^2}$$

although it is frequently approximated as the following.

$$S_M \approx \frac{\left|\frac{\partial f}{\partial x}\right| + \left|\frac{\partial f}{\partial y}\right|}{2}$$

The Sobel Magnitude Operator highlights pixels according to the difference between their brightness and the brightness of their neighbors. Since this operator is performed after the Logarithm filter applied in step 1, the resulting image will emphasize dark pockets on an otherwise dim background. After the Sobel Magnitude Operator is applied, the image will contain a number of bright 'rings' around the identified dark defects.
3. Invert Original Image: The original image captured by the camera is inverted so that bright pixels appear dark and dark pixels appear bright. This results in an image with dark defect areas appearing as bright spots.
4. Multiplication: The image obtained after step 2 is multiplied with the image obtained after step 3. Multiplication of two images like this is functionally equivalent to performing an AND operation on them. Only pixels which appear bright in both of these images will appear bright in the resultant image. In this case, the multiplication of these two images will result in the highlighting of the rings found in step two, but only if these rings surround a dark spot.
5. Threshold: All pixels with a brightness below a specified value are set to OFF while all pixels greater than or equal to the specified value are set to ON.
6. Fill in Holes: The image obtained after the completion of steps 1-5 appears as a series of ON-pixel rings. The final step is to fill in all enclosed contours with ON pixels.

After completing these steps, the resultant image should consist of a pixels corresponding to potential defects. These bright blobs are superimposed on areas that originally contained dark defects.

Bright Defects

The detection of bright defects is a two step process.
1. Threshold: A pixel brightness threshold filter may be applied to pick out all saturated pixels (grayscale 255). A user-definable threshold may be provided so values lower than 255 can be detected.
2. Count Filter: A count filter is a technique for filtering small pixel noise. A size parameter is set (2, 3, 4, etc) and a square box is constructed whose sides are this number of pixels in length. Therefore, if the size parameter is set to 3, the box will be 3 pixels by 3 pixels. This box is then centered on every pixel picked out by the threshold filter applied in step 1. The filter then counts the number of additional pixels contained within the box which have been flagged by the threshold filter and verifies that there is at least one other saturated pixel present. Any pixel which fails this test has its brightness set to 0. The effect of this filter operation is to blank out isolated noise pixels.

Once these two steps have been completed, the resultant binary image will consist of ON pixels corresponding to potential defects. Furthermore, any 'speckling' type noise in the original image which would have resulted in an ON pixel will have been eliminated leaving only those pixels which are in close proximity to other pixels which are ON.

Pixel Count

After bright and/or dark defect detection algorithms have been run in a given region, the resultant processed images are binary. These two images are then OR'ed together. This results in a single image with both bright and dark defects.

Figure 25:
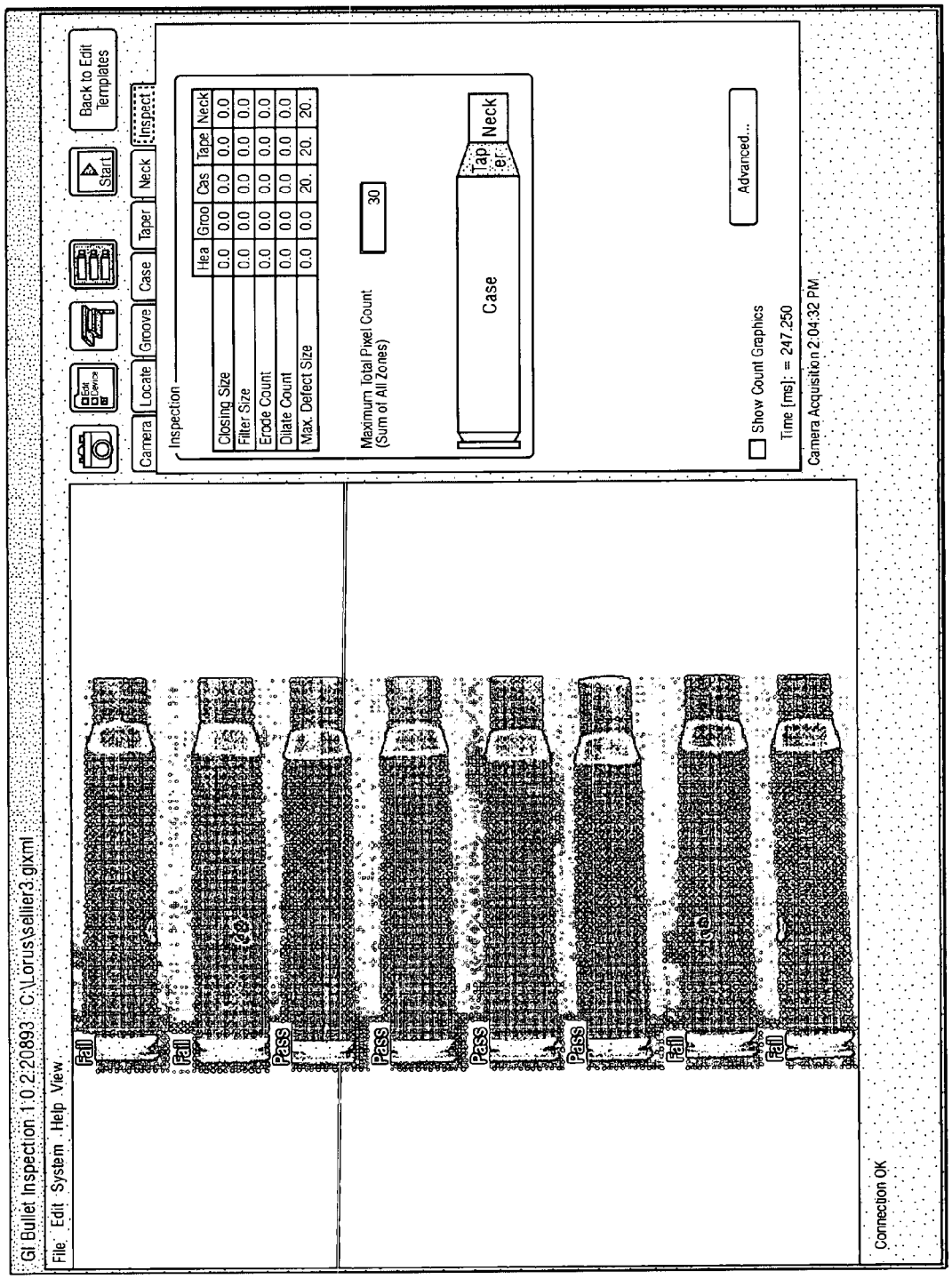
FIG. 25 is a schematic view of a screenshot which illustrates various bullets which have either passed or failed the inspection.

The software now counts the number of ON pixels in each detected defect. Finally, the part will be flagged as defective if either the quantity of defect pixels within a given connected region is above a user-defined threshold, or if the total quantity of defect pixels across the entire part is above a user-defined threshold. The final outcome of this process is shown in FIG. 25, overlaid on top of the original images.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method for inspecting manufactured parts and sorting the inspected parts, the method comprising:
   consecutively conveying the parts so that the parts travel along a path which extends through a plurality of inspection stations including a circumference vision station;
   illuminating a plurality of annular, exterior side surfaces of a part evenly when the part is located in the circumference vision station with rings of strobed radiation to generate corresponding reflected radiation signals;
   imaging the reflected radiation signals to generate a plurality of side images;
   allowing the part to fall freely so that the part is unconfined and unobstructed during the steps of illuminating and imaging;
   processing the side images of each part to identify parts having an unacceptable defect;
   directing parts identified as having an unacceptable defect to a defective part area; and
   directing parts not identified as having an unacceptable defect to an acceptable part area.

2. The method as claimed in claim 1, wherein the rings of the strobed radiation have different angles of incidence with respect to their respective illuminated side surfaces.

3. The method as claimed in claim 1, wherein the parts include cartridge cases and wherein a top surface of each case is located at a mouth end of the case and a bottom surface of each case is located at a primer end of the case.

4. The method as claimed in claim 1, wherein the inspection stations include a gauging station and wherein the method further comprises:
   measuring at least one geometric dimension of a part when the part is located in the gauging station; and
   processing the at least one geometric dimension to identify parts having an unacceptable defect.

5. The method as claimed in claim 3, wherein the inspection stations include a mouth vision station, and wherein the method further comprises:
   generating a top image of each case located at the mouth vision station; and
   processing the top image to determine at least one of a split, a fold, a dent, an out-of-round condition, inner diameter and outer diameter located at the mouth end of each case.

6. The method as claimed in claim 3, wherein the side images are processed during the step of processing to determine at least one of a dent, a split, a perforation, a crack, a scratch, a wrinkle, a buckle, a bulge and a surface blemish located at the side surfaces of the case.

7. The method as claimed in claim 3, wherein the inspection stations include a primer vision station, and wherein the method further comprises:
   generating a bottom image of each case locate at the primer vision station; and
   processing the bottom image to determine at least one of a split, a crack, flash-hole presence, primer absence, a cocked primer, primer pocket diameter and an inverted primer located at the primer end of each case.

8. The method as claimed in claim 1, wherein upon identification of a defective part, directing the defective part to a defective part area prior to conveying the defective part through any further inspection stations.

9. The method as claimed in claim 1, wherein the parts are at least conductive or semiconductive, wherein the inspection stations include an eddy current station and wherein the method further comprises:
   generating an electromagnetic signature of a part when the part is located in the eddy current station; and
   processing the signature to identify parts having an unacceptable defect.

10. A system for inspecting manufactured parts and sorting the inspected parts, the system comprising:
    a conveyor subsystem;
    a feeder subsystem for feeding parts to the conveyor subsystem, wherein the feeder subsystem and the conveyor subsystem consecutively convey the parts so that the parts travel along a path which extends through a plurality of inspection stations including a circumference vision station;
    an illumination assembly for evenly illuminating a plurality of annular, exterior side surfaces of a part when the part is located in the vision station with rings of strobed radiation to generate corresponding reflected radiation signals;
    a plurality of imaging detectors located at the vision station, each of the detectors having an image plane for imaging the reflected radiation signals to generate a plurality of side images wherein the illumination assembly includes a plurality of ringlights having central apertures sized and aligned to allow the parts to fall freely and travel unsupported through the plurality of ringlights so that the parts are unconfined and unobstructed during illumination by the illumination assembly and imaging by the imaging detectors at the vision station and;
    at least one side image processor for processing the side images of each part to identify parts having an unacceptable defect;
    means including a part sorter for directing parts identified as having an unacceptable defect to a defective part area and directing parts not identified as having an unacceptable defect to an acceptable part area; and
    a system controller coupled to each of the inspection stations, the illumination assembly and the part sorter for controlling the sorting based on the inspecting.

11. The system as claimed in claim 10, wherein each of the ringlights has an axis and wherein each of the ringlights emits radiation in the form of a cone of radiation having a vertex located on its respective axis to evenly illuminate the annular, exterior side surfaces of the part while the part is in free fall.

12. The system as claimed in claim 10, wherein the parts include cartridge cases and wherein a top surface of each case is located at a mouth end of the case and a bottom surface of each case is located at a primer end of the case.

13. The system as claimed in claim 10, wherein the system is a small and medium caliber ammunition inspection and sorting system.

14. The system as claimed in claim 10, wherein the inspection stations include a gauging station and wherein the system further comprises:
    a non-contact gauging subsystem for measuring at least one geometric dimension of a part when the part is located in the gauging station to obtain measurement signals; and
    a signal processor for processing the measurement signals to identify parts having an unacceptable defect.

15. The system as claimed in claim 12, wherein the inspection stations include a mouth vision station and wherein the system further comprises:
    means including an imaging detector for generating a top image of each case located at the mouth vision station; and
    a top image processor for processing the top image to determine at least one of a split, a fold, an out-of-round condition, inner diameter, outer diameter and a dent located at the mouth end of each case.

16. The system as claimed in claim 12, wherein the side images are processed by the at least one side image processor to determine at least one of a dent, a split, a perforation, a crack, a scratch, a wrinkle, a buckle, a bulge and a surface blemish located at the side surfaces of the case.

17. The system as claimed in claim 12, wherein the inspection stations include a primer vision station and wherein the system further comprises:
    means including an imaging detector for generating a bottom image of each case located at the primer vision station; and
    a bottom image processor for processing the bottom image to determine at least one of a split, a crack, flash-hole presence, primer absence, a cocked primer, primer pocket diameter and an inverted primer located at the primer end of each case.

18. The system as claimed in claim 10 further comprising an actuator coupled to the system controller wherein upon identification of a defective part, the controller controls the actuator to direct the defective part to a defective part area prior to conveying of the defective part through any further inspection stations.

19. The system as claimed in claim 10, wherein the parts are at least conductive or semiconductive, wherein the inspection stations include an eddy current station and wherein the system further comprises:
    an eddy current subsystem for generating an electromagnetic signature of a part when the part is located in the eddy current station; and
    a signature processor for processing the signature to identify parts having an unacceptable defect.

* * * * *

UNITED STATES PATENT AND TRADEMARK OFFICE
CERTIFICATE OF CORRECTION

| | | |
|---|---|---|
| PATENT NO. | : 7,403,872 B2 | Page 1 of 1 |
| APPLICATION NO. | : 11/786973 | |
| DATED | : July 22, 2008 | |
| INVENTOR(S) | : St. Onge et al. | |

It is certified that error appears in the above-identified patent and that said Letters Patent is hereby corrected as shown below:

Column 20, Line 4, Claim 7:

Delete "locate" and insert -- located --.

Signed and Sealed this

Sixteenth Day of December, 2008

JON W. DUDAS
*Director of the United States Patent and Trademark Office*